US011375752B1

(12) United States Patent
Bajpai et al.

(10) Patent No.: US 11,375,752 B1
(45) Date of Patent: Jul. 5, 2022

(54) PORTABLE ELECTRONIC VAPORIZER HAVING REMOVABLY ATTACHABLE VAPORIZATION MODULE AND DEVICE, REMOVABLY ATTACHABLE BASE PORTION, AND METHOD

(71) Applicant: Puff Corporation, Los Angeles, CA (US)

(72) Inventors: Avinash Bajpai, La Crescenta, CA (US); Siddhant Waghmare, Los Angeles, CA (US)

(73) Assignee: Puff Corporation, Los Angeles, CA (US)

( * ) Notice: Subject to any disclaimer, the term of this patent is extended or adjusted under 35 U.S.C. 154(b) by 0 days.

(21) Appl. No.: 17/407,446

(22) Filed: Aug. 20, 2021

Related U.S. Application Data

(60) Provisional application No. 63/185,458, filed on May 7, 2021.

(51) Int. Cl.
*A24F 40/46* (2020.01)
*A24F 40/48* (2020.01)
*A24F 40/42* (2020.01)

(52) U.S. Cl.
CPC .............. *A24F 40/46* (2020.01); *A24F 40/42* (2020.01); *A24F 40/48* (2020.01)

(58) Field of Classification Search
CPC .......... A24F 40/40; A24F 40/42; A24F 40/46; A24F 40/48; A24F 5/00
See application file for complete search history.

(56) References Cited

U.S. PATENT DOCUMENTS

| 10,231,483 B2 * | 3/2019 | Garcia ...................... A24F 5/00 |
| 10,321,714 B1 | 6/2019 | Kane |
| 10,357,058 B1 * | 7/2019 | Contreras ................. F23Q 7/16 |
| 10,517,334 B1 | 12/2019 | Volodarsky et al. |
| 10,517,338 B2 | 12/2019 | Volodarsky et al. |
| 2009/0071481 A1 | 3/2009 | Fishman |
| 2013/0087160 A1 * | 4/2013 | Gherghe ................. A24F 40/44 131/329 |
| 2013/0319437 A1 | 12/2013 | Liu |

(Continued)

FOREIGN PATENT DOCUMENTS

DE 102016012830 8/2017

OTHER PUBLICATIONS

Puff Co., Peak Atomizer Assembly posted on Instagram retrieved from www.instagram.com/p/BfMk5MKIBp1/ Feb. 14, 2018.

(Continued)

*Primary Examiner* — Hae Moon Hyeon
(74) *Attorney, Agent, or Firm* — Bryan Cave Leighton Paisner LLP

(57) ABSTRACT

The present invention relates to a portable electronic vaporizing device that provide an enhanced vaporizing experience, including vaporizers with improved quality of the vapor produced for inhalation and improved ease of use. The portable electronic vaporizing device comprises a removably attachable vaporization module, and a mouthpiece configured to receive a flow of gas having vaporized product entrained therein from the removably attachable vaporization module. Methods of using such a device and a removably attachable vaporization module that is compatible with the device are also provided.

25 Claims, 20 Drawing Sheets

(56) References Cited

U.S. PATENT DOCUMENTS

| | | |
|---|---|---|
| 2014/0083441 A1 | 3/2014 | Kaplani |
| 2015/0122275 A1 | 5/2015 | Wu |
| 2015/0165137 A1 | 6/2015 | Mullinger et al. |
| 2016/0100628 A1* | 4/2016 | Garcia ................ A24F 1/00 131/328 |
| 2016/0219937 A1 | 8/2016 | Rado |
| 2016/0302486 A1 | 10/2016 | Eroch |
| 2016/0366936 A1 | 12/2016 | Liu |
| 2017/0027224 A1 | 2/2017 | Volodarsky et al. |
| 2017/0055579 A1 | 3/2017 | Kuna |
| 2017/0055588 A1 | 3/2017 | Cameron |
| 2017/0079324 A1 | 3/2017 | Eksouzian |
| 2017/0251718 A1 | 9/2017 | Armoush |
| 2017/0295845 A1 | 10/2017 | Bajpai et al. |
| 2018/0098569 A1* | 4/2018 | Martin ................ A24F 42/20 |
| 2018/0125115 A1 | 5/2018 | Mueller |
| 2018/0271150 A1 | 9/2018 | Sparklin |
| 2019/0174825 A1 | 6/2019 | Neuhaus |
| 2020/0221768 A1 | 7/2020 | Volodarsky et al. |
| 2021/0045440 A1 | 2/2021 | Volodarsky et al. |

OTHER PUBLICATIONS

Puff Co., Peak Video posted on Instagram retrieved from www.instagram.com/p/Bd-oaEkFrXC/ Jan. 15, 2018.

Puff Co. Glass Attachment Video posted on Instagram retreived from www.instagram.com/p/Bd3DfMRIWLo/ Jan. 12, 2018.

Puff Co., Puffco Peak Case posted on Instagram retrieved from www.instagram.com/p/Bd027vflYzM/ Jan. 11, 2018.

Puff Co., Puffco Peak Video posted on Instagram retrieved from www.instagram.com/p/BdtMs4qlHnH/ Jan. 8, 2018.

Puff Co., Puffco Peak Hero Shot posted on Instagram retrieved from www.instagram.com/p/BdybEMAI_zX/ Jan. 10, 2018.

PAX Labs, Inc., web page of vaporizers, retrieved from www.paxvapor.com Feb. 25, 2015.

Koerber, B., This weed company just made a smart bong and it's awesome, Mashable, located at mashable.com/2018/01/08/puffco-peak-smart-bong-dab-rig-concentrates/ Jan. 8, 2018.

Tarantola, A., The Puffco Peak vaporizer is a quick hit of concentrated genius, Engadget, located at www.engadget.com/2018/03/16/puffco-peak-vaporizer-hands-on/?guccounter=1 Mar. 18, 2018.

Puff Co., Reservations are now open for Peak Atomizer Assembly, retrieved from web.archive.org/web/20180224162936/https://www.puffco.com/ Feb. 24, 2018.

Engadget, Hands on Peak, retrieved from web.archive.org/web/20180330221034/https://www.engadget.com/2018/03/16/puffco-peak-vaporizer-hands-on/ Mar. 31, 2018.

Dr. Dabbler, Vaporizers for sale, retrieved from https://web.archive.org/web/20170222202821/https://drdabbervaporizersforsale.weebly.com/ Feb. 22, 2017.

Dr. Dabbler, Boost: Black Edition retrieved from www.drdabber.com/products/boost-black-edition 2019.

Dr. Dabbler, Boost Black Edition retrieved from www.drdabber.com/collections/all/products/boost-black-edition 2019.

Source Vapes, web page for Atomizers, retrieved from www.sourcevapes.com 2019.

Source Vapes, web page for Atomizers, retrieved from www.sourcevapes.com/collections/atomizers Feb. 16, 2016.

Vapexhale, Give the gift of relaxation, retrieved from www.xhl3.com Nov. 27, 2017.

Vapexhale, web page for starter kits, retrieved from www.xhl3.com 2019.

Cloud V Enterprises, Cloud V Bubbler Options, retrieved from cloudvapes.com/vaporizers/portable-enail/cloudv-electro-portable-dab-rig 2019.

Cloud V Enterprises, Ultra Slim Design Vaporizers, retrieved from cloudvapes.com/store/ Jan. 21, 2013.

Cloud V Enterprises, Cloud V, retrieved from cloudvapes.com/store/ Feb. 22, 2016.

Dabado Vaporizers, web page for Dabado Bolt, retrieved from dabadovaporizers.com/collections/bolts 2019.

Dabado Vaporizers, web page for Dabado Bolt, retrieved from dabadovaporizers.com Jan. 1, 2016.

Kevin H., Focusvape Tourist Review—The Accidental Tourist, retrieved from vapesterdam.com/review/focusvape-tourist-review/ 2019.

Focus Vape, web page of vaporizers, retrieved from focusvape.eu/shop/ Jul. 17, 2017.

PAX Labs, Inc., PAX 3, retrieved from paxvapor.com 2019.

Waxxim, Vape Pen Bubblers shopping page, retrieved from www.waxxim.com 2019.

Puff Co., Introducing the Peak, retrieved from vimeo.com/257080728 Feb. 28, 2018.

Patent Cooperation Treaty, International Search Report for PCT/US2019/013501, 6 pages Oct. 10, 2019.

Polar Bottle, Sport Cap, retrieved from polarbottle.com/product/bottles/free-replacement-cap/sport/ on Nov. 1, 2019 2019.

Lock & Lock, Lock & Lock, No BPA, Water Tight, Food Container, 2.5-cup, 20-oz, HPL933, retrieved from www.amazon.com/Water-Tight-Container-2-5-cup-HPL933/dp/B005BRGWZE on Nov. 1, 2019 Oct. 2014.

Smokea, Piecemaker Kahuna 2 in. Silicone Bong, retrieved from https://smokea.com/products/piecemaker-kahuna-2-silicone-bong?variant=37965420929 on Nov. 1, 2019 Jun. 2018.

Osprey, Hydraulics Bite Valve, retrieved from https://www.osprey.com/us/en/product/hydraulics-bite-valve-NONMAGVALV.html on Nov. 1, 2019 Apr. 2013.

Bray, Flowtek Triad Series, retrieved from www.bray.com/ball-valves/3-piece-valves/triad-series on Nov. 1, 2019 Mar. 2017.

Grenco Science, Gpen Connect Collection, retrieved from web.archive.org/web/20191001142752/https://www.gpen.com/collections/g-pen-connect Oct. 1, 2019.

Dr. Dabbler, Boost: Black Edition Support retrieved from web.archive.org/web/20210127091740/https://www.drdabber.com/pages/boost-black-support Jan. 27, 2021.

VapeYaya, e-pipe, retrieved from web.archive.org/web/20210509224114/https://www.vapeyaya.com/index.php?_route_=Premium-E-cig-E-Pipe May 9, 2021.

Pulsar Vaporizers, Pulsar Petite Pocket Carting Rig Bubbler, retrieved web.archive.org/web/20210331144200/https://www.pulsarvaporizers.com/products/pulsar-petite-pocket-cart-rig-bubbler-5 from Mar. 31, 2021.

Lookah, Lookah Q7 Mini Enail Banger Fits onto Water Pipes and Dab Rigs, retrieved from web.archive.org/web/20210124114528/https://www.lookah.com/vaporizers/dab-vaporizer/lookah-q7-water-pipe-compatible-concentrate-vaporizer.html Jan. 24, 2021.

EPuffer, Inc., ePuffer ePipe, retrieved from epuffer.com/news-and-press/epuffer-epipe-629x-flat-led-cap/ Apr. 4, 2020.

\* cited by examiner

PORTABLE ELECTRONIC VAPORIZER HAVING REMOVABLY ATTACHABLE VAPORIZATION MODULE AND DEVICE, REMOVABLY ATTACHABLE BASE PORTION, AND METHOD

FIELD OF THE INVENTION

Aspects of the present invention relate to portable electronic vaporizing devices for use with vaporizable products.

BACKGROUND

Electronic vaporizers are commonplace and are generally utilized for the purpose of aroma and/or inhalation therapy. In this regard, vaporizers heat a substance, herbs for example, such as tobacco, cannabis, lavender, chamomile, and many other types of plant material. The vaporizer may work by heating the substance through the use of direct heat or the use of hot air. There are three common ways of heating the substance. The first is thermal conduction where the substance is set directly on a heating element such as a ceramic or metal plate. The second is thermal radiation in which light is used to heat the substance. The third is convection where hot air is passed over the substance. Yet another suitable mechanism for vaporizing a substance may be via inductive heating.

At lower levels of heat, vapors extracted from substances such as vegetable materials are mainly aroma therapeutic (inactive fragrance) and do not usually contain the active ingredients of the substance. Without the active ingredients being present, there is no physiological reaction. At higher levels of heat, active ingredients will be increasingly included in the vapor given off during heating. Usually, aromatic vapors have already been released and are not always present at the higher heat levels. With some substances, such as cannabis, active ingredients appear at different levels of heat.

After the substance is heated a mist or vapor containing some aspect of the substance is released and either enjoyed as an aromatic or inhaled to obtain a physiological reaction. The warm air containing the substance product can be harsh on the throat and bronchial tubes. Accordingly, some vaporizers use a cooling down process that allows water moisture to be included in the vapor produced. These vaporizers enable the user to inhale a cool moist vapor that is relatively less harsh and irritating. Vaporizers are often preferred over traditional methods of heating or smoking substances due to the reduction of harsh side effects. Some of these side effects include inhalation of tar, carbon monoxide, and other carcinogens either directly or from second hand smoke. With many states imposing smoking bans in public areas, vaporizers have become popular substitutes.

Accordingly, there is a need for improved vaporizers that provide an enhanced vaporizing experience, including vaporizers with improved quality of the vapor produced for inhalation and improved ease of use.

SUMMARY

Aspects of the invention are directed to a portable electronic vaporizing device comprising a removably attachable vaporization module, and a mouthpiece configured to receive a flow of gas having vaporized product entrained therein from the removably attachable vaporization module. The mouthpiece comprises: a mouthpiece housing at least partly defining an interior chamber, an inhalation outlet formed in the mouthpiece housing, and a receiving area for receiving the removably attachable vaporization module that is battery powered, in the interior chamber of the mouthpiece housing. The removably attachable vaporization module comprises: a base portion and a vaporization assembly. The base portion comprises: a module housing having an insert portion configured to be at least partly received within the receiving area of the mouthpiece housing, the insert portion having one or more sealing regions configured to form a seal between the module housing and the mouthpiece housing, and a battery receiving area disposed within the insert portion and configured to receive a battery for powering the removably attachable vaporization module, and a gas flow conduit having an input opening and an output opening positioned to output the flow of gas from the removably attachable vaporization module to the receiving area of the mouthpiece at an interior side of the seal between the module housing and the mouthpiece housing. The vaporization assembly comprises: a vaporization assembly housing, a refillable container configured to receive a vaporizable product within the vaporization assembly housing, a heating device configured to be electrically connected to the battery and transfer energy to the vaporizable product in the refillable container to heat the vaporizable product and form a vaporized product therefrom, an inlet configured to introduce gas into the refillable container, one or more refillable container outlets configured to receive the flow of gas having vaporized product entrained therein from the refillable container, and one or more vaporization assembly outlets configured to provide the flow of gas received from the refillable container outlets to the input opening of the gas flow conduit in the base portion. In operation of the portable electronic vaporizing device, the flow of gas having the vaporized product entrained therein is passed through the gas flow conduit and received into the receiving area of the mouthpiece from the output opening of the gas flow conduit, and is passed along the interior chamber of the mouthpiece to the inhalation outlet.

According to another aspect of the invention, a method of using the portable electronic vaporizing device disclosed herein is provided. The method comprises: inserting the removably attachable vaporization module into the receiving area of the mouthpiece; providing vaporizable product to the refillable container of the removably attachable vaporization module; activating the heating device to heat the vaporizable product in the refillable container to at least partly vaporize the product; and inhaling gas entrained with the vaporizable product from the inhalation outlet of the mouthpiece.

According to yet another aspect of the invention, a removably attachable base portion of a vaporization module is provided for vaporizing a vaporizable product in a portable vaporizing device having a receiving body to receive the removably attachable base portion in a receiving area thereof. The removably attachable base portion comprises: a housing having an insert portion configured to be at least partly received within the receiving area of the receiving body, the insert portion having one or more sealing regions configured to form a seal between the housing and one or more walls of the receiving body, and a battery receiving area disposed within the insert portion and configured to receive a battery for powering the vaporization module; and a gas flow conduit having an output opening positioned to output the flow of gas from the removably attachable base portion to the receiving area of the receiving body at an interior side of the seal between the housing and the one or more walls of the receiving body.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Aspects of the invention as described herein are directed to an improved portable electronic vaporizing device for the inhalation of vaporizable substances, such as aromatic substances, therapeutic substances and/or substances with physiological effects. Examples of such substances can include herbs, such as tobacco, cannabis, lavender, chamomile, and other types of plant material. In one embodiment, a vaporizable substance can comprise a cannabinoid, such as for example one or more of cannabadiol (a generally non-psychoactive therapeutic substance) and tetrahydrocannabinol (THC) (a psychoactive therapeutic substance). The vaporizable substance may in some embodiments be in the form of an oil and/or wax product comprising the vaporizable substance, e.g., as extracted from plant material containing the substance, and may optionally be provided in combination with carriers or other additives.

Figure 1:
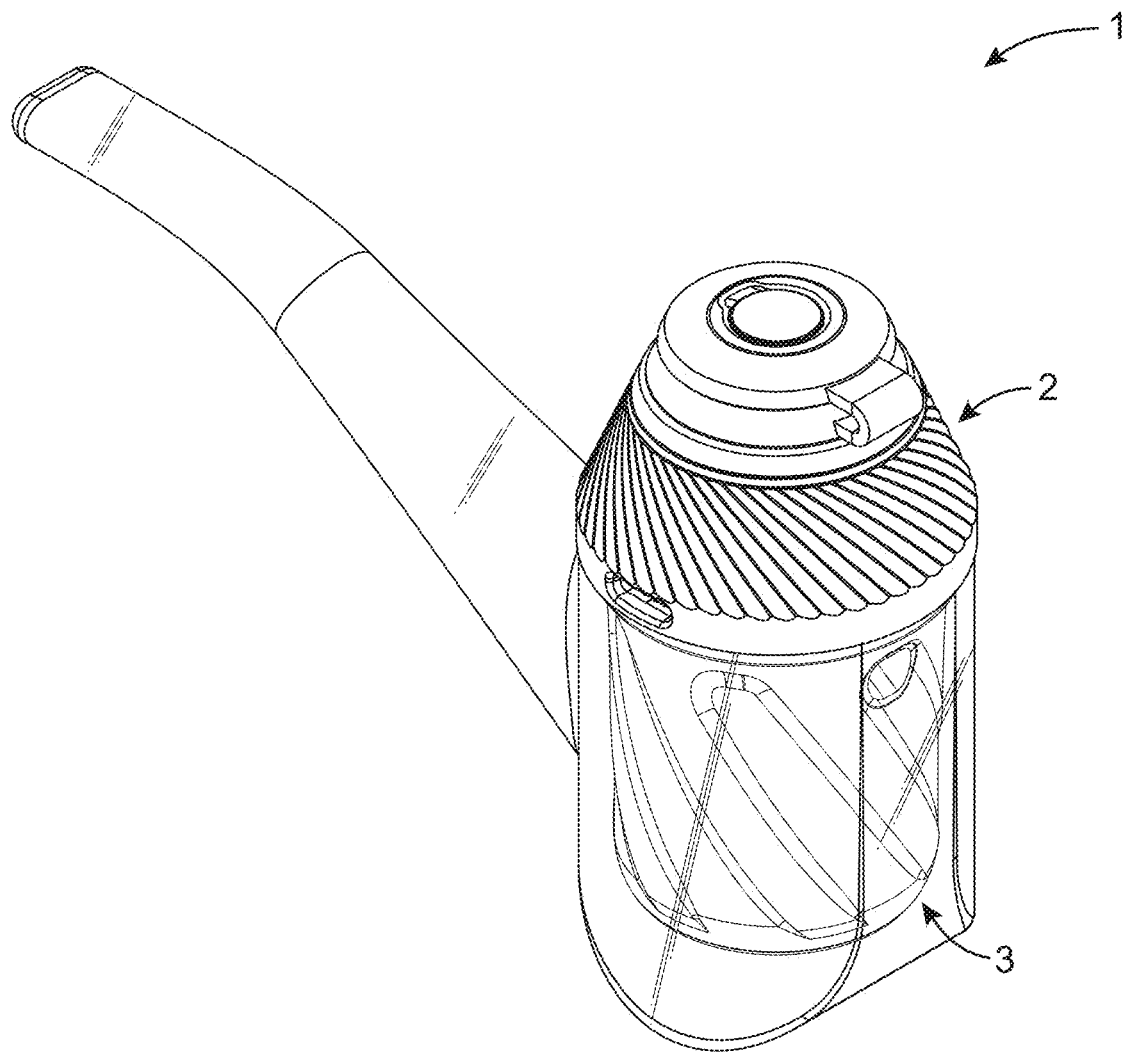
FIG. 1 shows an embodiment of a portable electronic vaporizing device comprising a removably attachable vaporization module and a mouthpiece.

Referring to FIG. 1, an embodiment of a portable electronic vaporizing device 1 is shown according to aspects of the disclosure herein. The portable electronic vaporizing device 1 comprises a removably attachable vaporization module 2 and a mouthpiece 3. The removably attachable vaporization module 2 is configured to receive a vaporizable product therein and to heat the vaporizable product to form a vapor therefrom. The mouthpiece 3 comprises an inhalation outlet 305 where a user can inhale the vapor produced by the removably attachable vaporization module 2, optionally with water or other substances entrained therein. The mouthpiece 3 can be provided in various forms including but not limited to a pipe, or forms, and optionally with water filtration.

Figure 2:
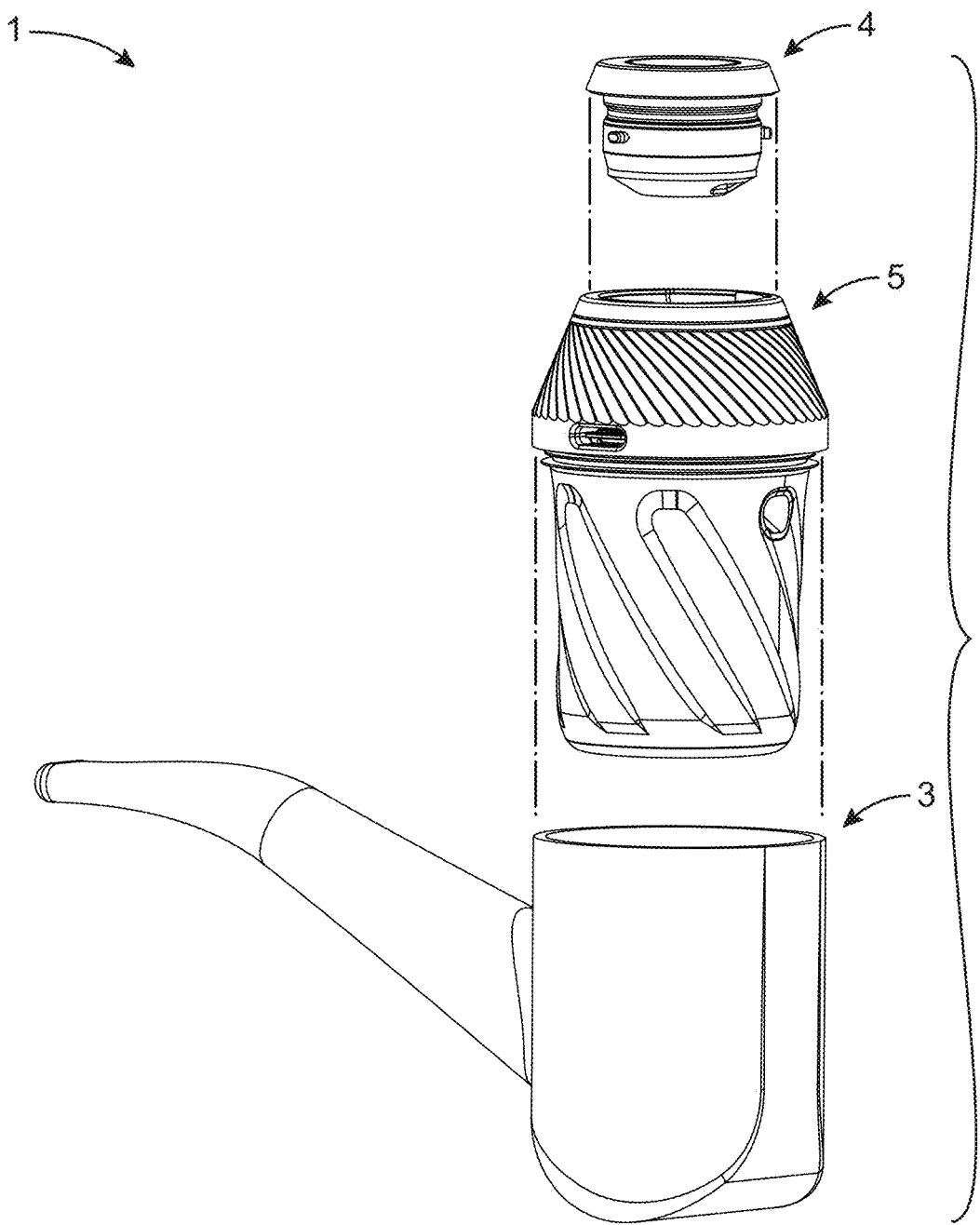
FIG. 2 is an exploded side view of an embodiment of the device.

Referring to FIG. 2, an embodiment of the device 1 is shown in exploded view, with the removably attachable vaporization module 2 removed from the mouthpiece 3. The removably attachable vaporization module 2 further comprises (and in FIG. 2 is shown as separated into) a vaporization assembly 4 and a base portion 5. The base portion 5 provides a gas flow connection between the vaporization assembly 4 and mouthpiece 3, to deliver the vaporized product from the vaporization assembly 4 to the mouthpiece 3 for delivery to the user via inhalation thereof. The base portion 5 can also comprise a housing for one or more components for powering and/or controlling the device 1. For example, the base may contain compartments therein for storing a power source, such as a battery, for powering elements of the device 1 such as a heating element or other heating device used in the vaporization assembly 4. In a case where the device is powered by a rechargeable battery, such as a lithium ion battery, the base portion 5 may also comprise a charging port connectable to a battery charger (not shown). The base may also have compartment doors to allow access to a battery or other components held within the housing. The base portion 5 may also house further control circuitry for controlling the device, such as to provide predetermined heating cycles or heating programs, and may also allow for user interaction with the device via control buttons and/or control interface, a display and/or lights to signal to the user, and/or other control and operation features.

In one embodiment, the mouthpiece 3 is removably attachable to the base portion 5, for example so as to allow a user to readily remove the mouthpiece for cleaning and/or replacement, as is described in further detail herein. For example, according to one embodiment, the base portion 5 and mouthpiece can be removed from one another by exerting a force on the base portion 5 that exceeds a retaining force of sealing regions (described below) that form a seal between portions of the base portion and the mouthpiece), to lift the base portion 5 out of the mouthpiece. The base portion 5 can be re-attached to the mouthpiece by inserting the insert portion (described below) into the receiving area of the mouthpiece and engaging the sealing regions to retain the base portion 5 as inserted within the mouthpiece. Other mechanisms for removably attaching the base portion 5 to the mouthpiece can also be provided. In yet another embodiment, the vaporization assembly 4 may be removably attachable to the base portion 5, for example so as to allow a user to replace the vaporization assembly 4 when no longer serviceable, for cleaning of the vaporization assembly 4, and/or to more readily allow access to a container (e.g. bowl) where a vaporizable product may be loaded into the vaporization assembly 4. For example, the vaporization assembly may be received in a vaporization assembly receiving area 506 of the base portion 5, and can be attached to the base portion 5 by twisting to engage a chamber bayonet 514 that secures the vaporization assembly in the receiving area 506. The vaporization assembly can be removed by untwisting to release from the chamber bayonet.

Figure 3A:
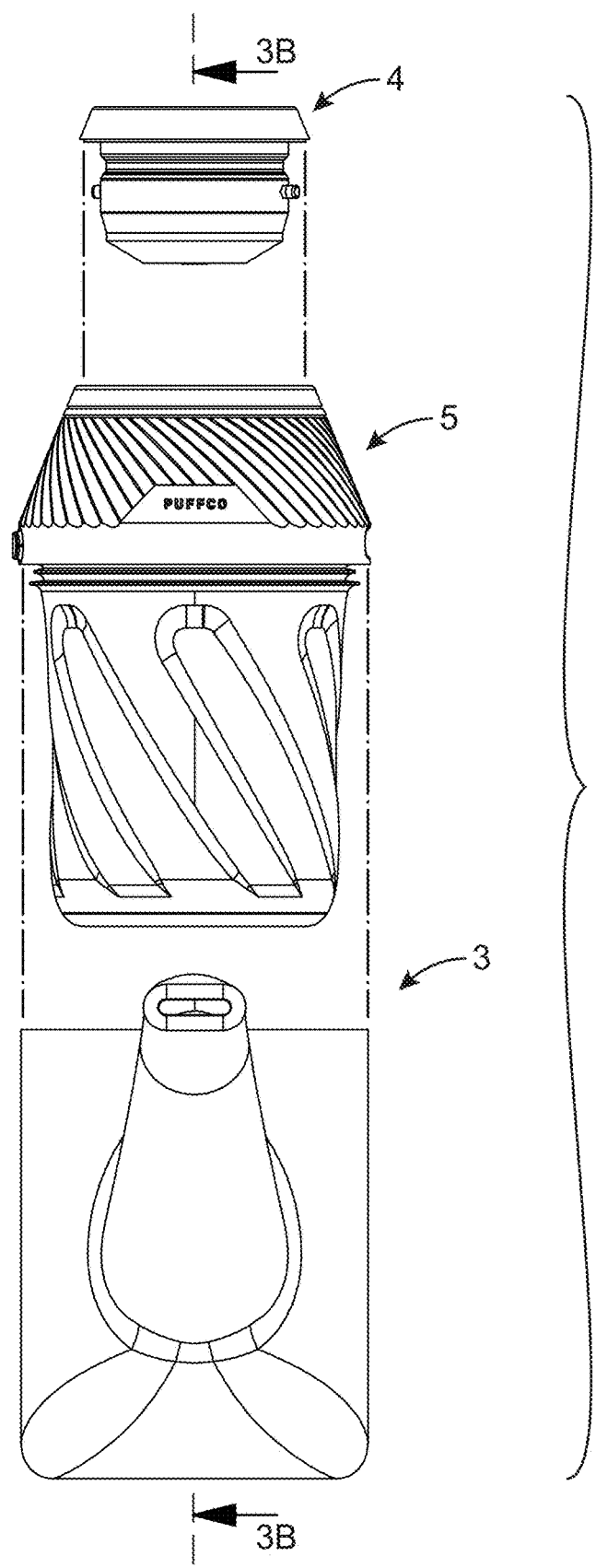
FIG. 3A is an exploded front view of the device of FIG. 2.

Other mechanisms for removably attaching the vaporization assembly to the base portion can also be provided. In one embodiment, both the vaporization assembly 4 and the mouthpiece 3 may be removably attachable to the base portion 5. In yet another version, the vaporization assembly 4 may be independently removable from the base portion 5. That is, the vaporization assembly 4 may be configured to be removably attached to the base such that it can be removed therefrom, without requiring that the mouthpiece 3 and/or base portion 5 be removed from one another beforehand. A cross-section view of the device 1 in exploded view can be found in FIG. 3B (FIG. 3A shows a front exploded view).

Figure 5A:
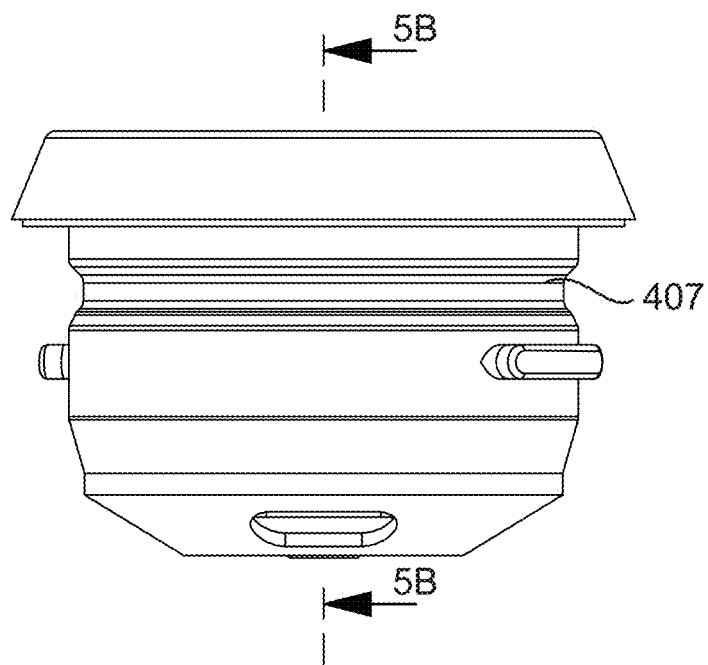
FIG. 5A is a perspective view of the vaporization assembly of FIGS. 4A-4E.
Figure 5B:
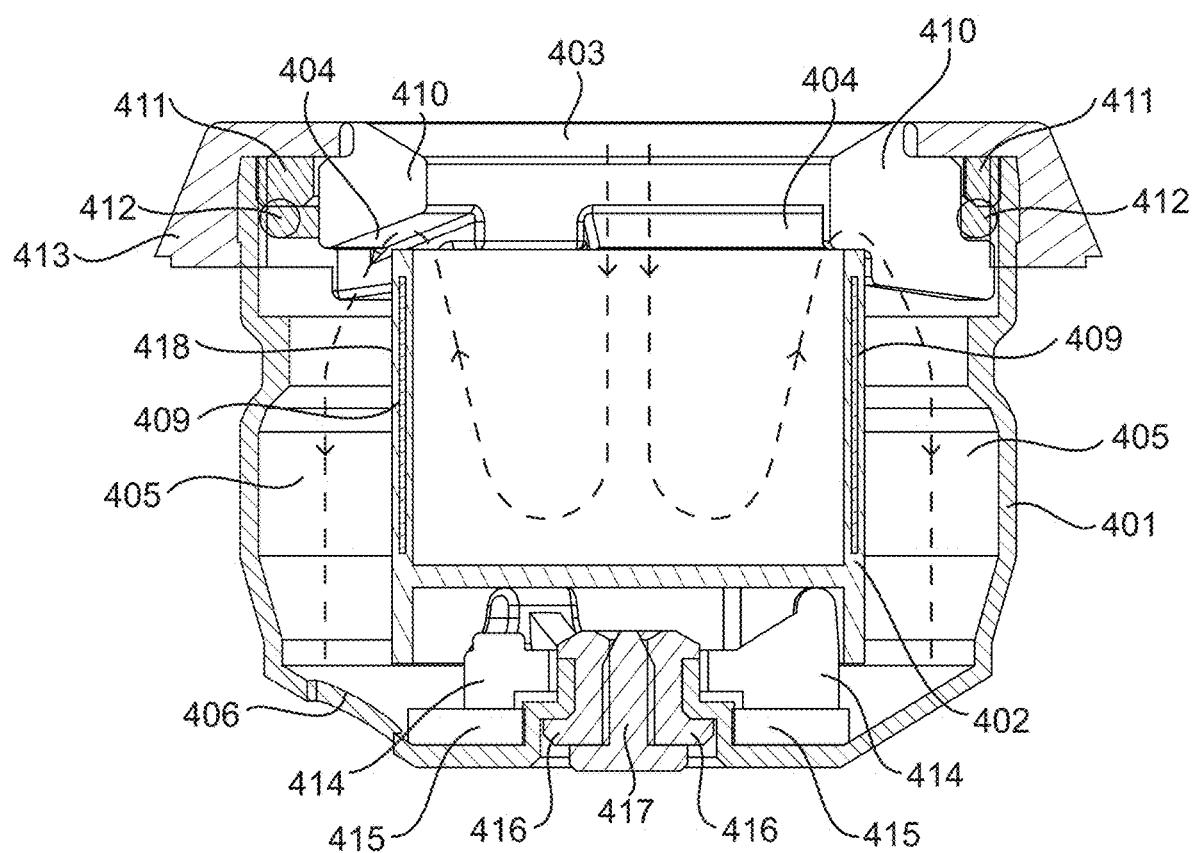
FIG. 5B is a cross-sectional view of FIG. 5A.

Referring to FIGS. 4A-4E, an embodiment of the vaporization assembly 4 is shown. Front and cross-sectional views of the structure of the vaporization assembly 4 and a gas flow path therethrough are shown in more details in FIGS. 5A-5B. According to one aspect of this disclosure, the vaporization assembly 4 as shown in FIGS. 4A-4E and 5A-5B is suitable for inhaling a vaporizable substance in the form of an oil and/or wax product comprising the vaporizable substance, e.g., as extracted or otherwise obtained from plant material containing the substance, and may optionally be provided in combination with carriers or other additives. Accordingly, the vaporization assembly 4 comprises a vaporization assembly housing 401, a refillable container 402 configured to receive a vaporizable product within the vaporization assembly housing 401, a heating device 409 configured to be electrically connected to a power source such as a battery and transfer energy to the vaporizable product in the refillable container 402 to heat the vaporizable product and form a vaporized product therefrom, an inlet 403 configured to introduce gas into the refillable container 402, one or more refillable container outlets 404 configured to receive a flow of gas having the vaporized product entrained therein from the refillable container 402, and one or more vaporization assembly outlets 406 configured to provide the flow of gas received from the refillable container outlets to the input opening 510 of the gas flow conduit 505 in the base portion. In one embodiment, the refillable container 402 itself comprises the heating device, such that the refillable container 402 can be directly heated to transfer energy to the vaporizable product therein, and thus no separate heating device is required. For example, sidewalls 418 of the refillable container 402 can comprise a resistive heating element (heater traces, as shown in FIG. 5B via dotted lines) embedded therein, e.g., by wrapping the heating element with soft ceramic material and forming a tube shape, adhering a thin ceramic bottom (without traces) to the tube, then firing the soft ceramic with heating element embedded therein to obtain the refillable container 402. In another embodiment, the bottom of the refillable container 402 may also comprise heating element (heater traces) embedded therein.

In one embodiment, the heating device 409 (heating element or heater trace) is attached to conductive elements such as wires leading to the power source (e.g. battery) in the base portion 5 to provide an applied voltage for the resistive heating. For example, in operation, two wires come from the bottom of the vaporization assembly 4: one of the wires can be held (pressed) between the electrode 417 and the insulator 416, being connected to the heating device 409 embedded in the sidewalls 418, and the other wire can be held between the insulator 416 and the housing 401, traveling up the housing wall and being spot welded to the housing 401. To apply the voltage, the base electrodes 517 contact the vaporization assembly housing 401 and the electrode 417, therefore a current path in and out of the heating device 409 can be created. There can be also grooves cut into the inner surface of the vaporization assembly housing to position these wires.

In yet another embodiment, the heating device is provided separately and/or apart from the container in any suitable form such as a heating plate or coil, and which can be placed in thermal contact with the refillable container 402 at any desirable position/angle such as being disposed below the bottom of the container. For example, the heating device may comprise at least one of a heating plate, a heating ring, and a heating element, and is capable of conductively heating the vaporizable product in the refillable container. As another example, the heating device may comprise an inductively heating device capable of inductively heating the container, and/or may be capable of radiatively heating the container and/or product provided within the container. In one embodiment, the heating element comprises a ceramic heating plate, such as an alumina plate, and may also comprise, e.g. a metal wire, coil, or other element that is capable of resistively heating, and which may also be embedded in a ceramic or glass heating plate or used alone. Additional embodiments of heating elements, heating plates and any other heating structures that can be used to form all or a part of the heating device 409 have been described in U.S. Pat. No. 10,517,334, which is hereby incorporated by reference herein in its entirety.

In yet another embodiment, the inlet 403 and the one or more refillable container outlets 404 of the vaporization assembly 4 are located towards a top of the refillable container 402 and the one or more refillable container outlets 404 of the vaporization assembly 4 are located radially external to the inlet 403 of the refillable container 402.

In one embodiment, the internal gas flow passage 405 is defined between the vaporization assembly housing 401 and walls of the refillable container 402, radially external to the refillable container 402, and the internal gas flow passage 405 redirects the flow of gas received from the one or more refillable container outlets 404 in a direction towards the base portion 5 of the battery powered, removably attachable vaporization module 2. As shown in FIG. 5B, the dashed lines illustrate an exemplary gas flow path within the vaporization assembly 4. A flow of ambient air enters the vaporization assembly 4 through the inlet 403, carries the vapor formed by the heated vaporable product in the refillable container 402, then passes through one or more refillable container outlets 404 located near the top edge of the refillable container 402 and enters into the internal gas flow passage 405, and eventually leaves the vaporization assembly 4 through one or more vaporization assembly outlets 406. In one embodiment, the one or more vaporization assembly outlets 406 is located at a lower region (e.g., the bottom) of the vaporization assembly housing 401. In yet another embodiment, at least one of the one or more vaporization assembly outlets 406 is aligned with the input opening 510 of the gas flow conduit 505 in the base portion 5.

According to embodiments herein, as shown in FIG. 5B, the vaporization assembly 4 can comprise a thermal spacer 410, a securing ring 411, an O-ring 412, a jacket 413, a bowl spacer 414, a washer 415, an insulator 416 and an electrode 417 to conduct electricity to the heating device 409.

Referring to FIGS. 6A-6E, an embodiment of the base portion 5 is shown. A cross-sectional view of the structure of the vaporization assembly 4 and base portion 5 with the gas flow path therethrough is shown in more detail in FIG. 7B. The base portion 5 comprises sidewalls 507 and a bottom wall 508 defining a vaporization assembly receiving area

Figure 6A:
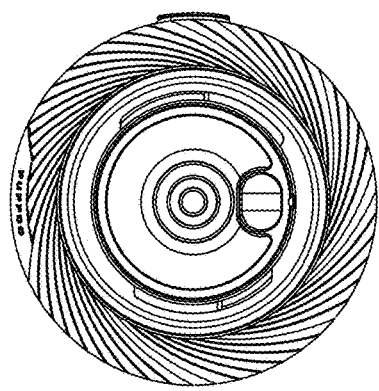
FIGS. 6A-6E show various views of an embodiment of a base.
Figure 6B:
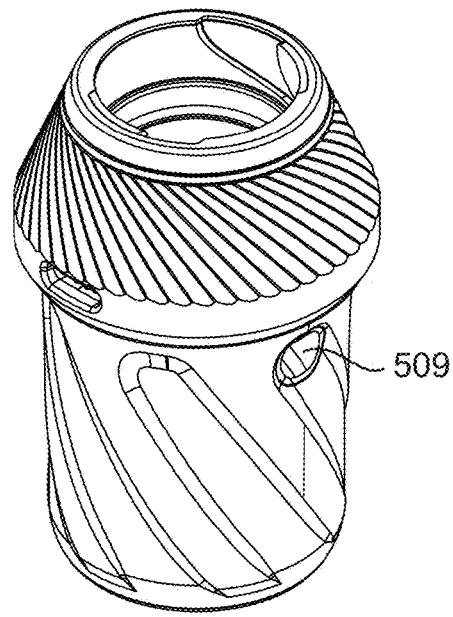
Figure 6C:
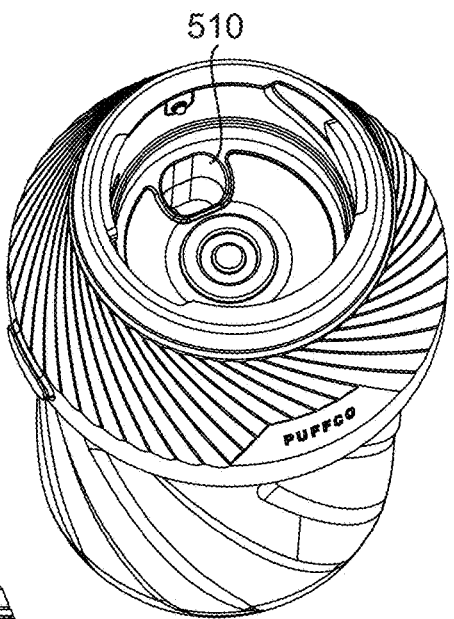
Figure 6D:
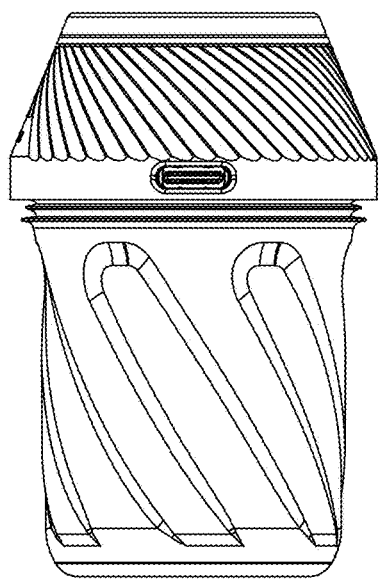
Figure 6E:
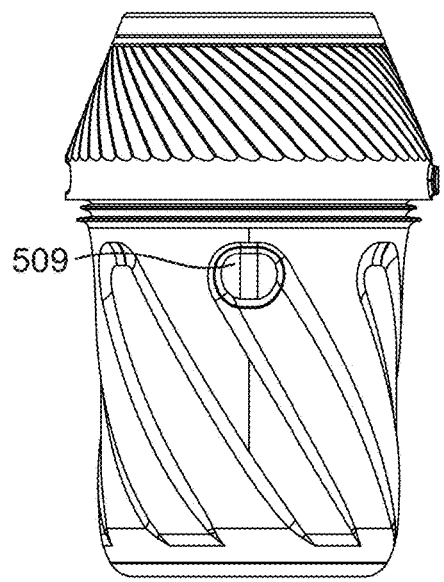
Figure 7A:
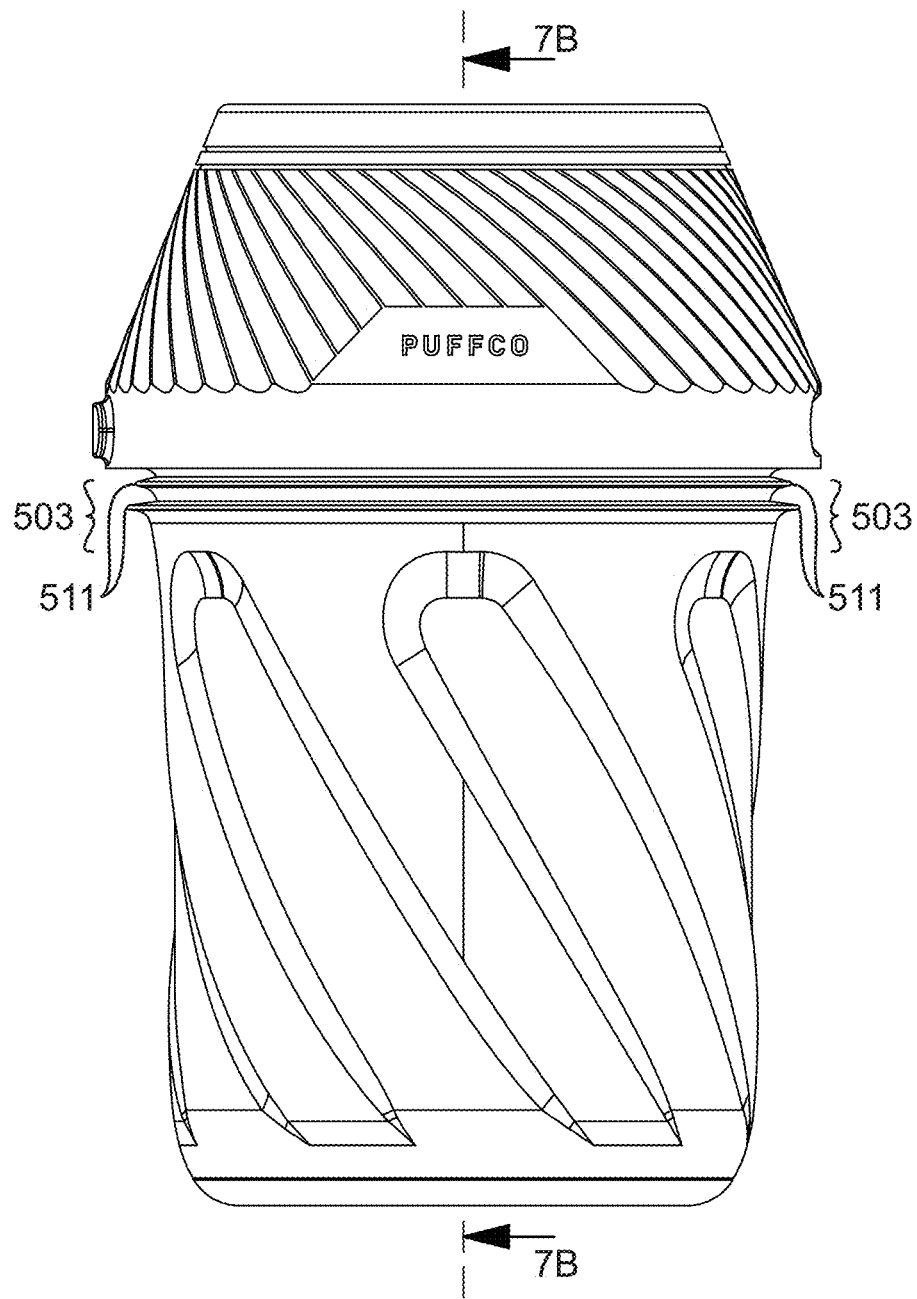
FIG. 7A is a perspective view of the base portion of FIGS. 6A-6E.
Figure 7B:
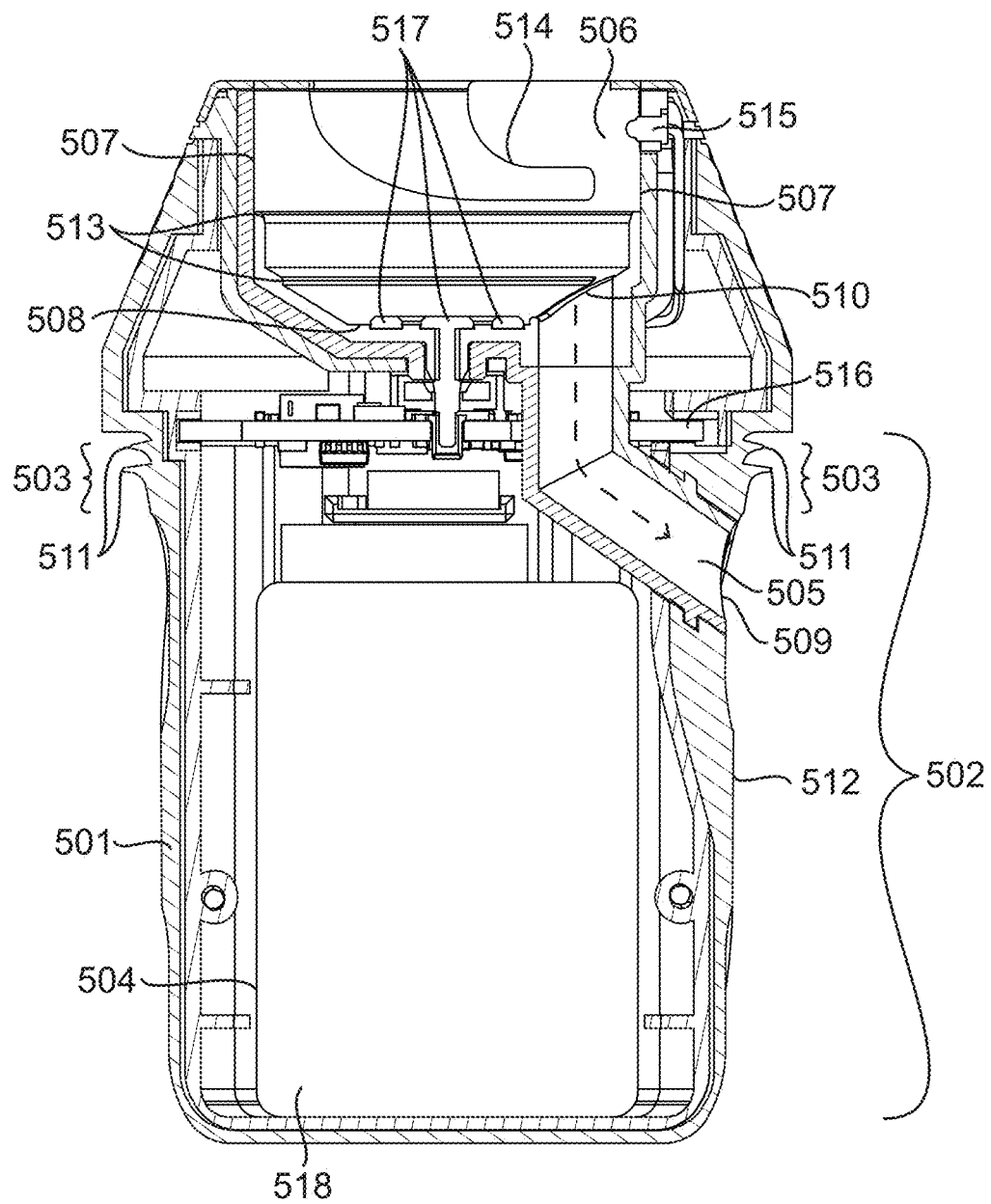
FIG. 7B is a cross-sectional view of FIG. 7A.
Figure 8A:
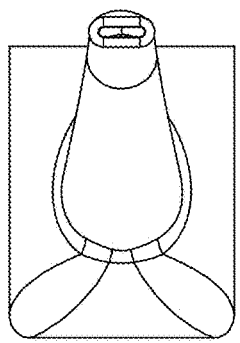
FIGS. 8A-8E show various views of an embodiment of a mouthpiece.
Figure 8B:
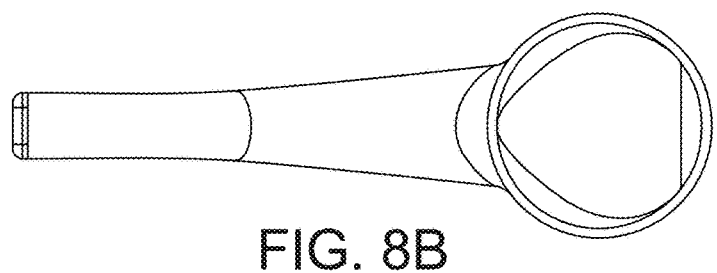
Figure 8C:
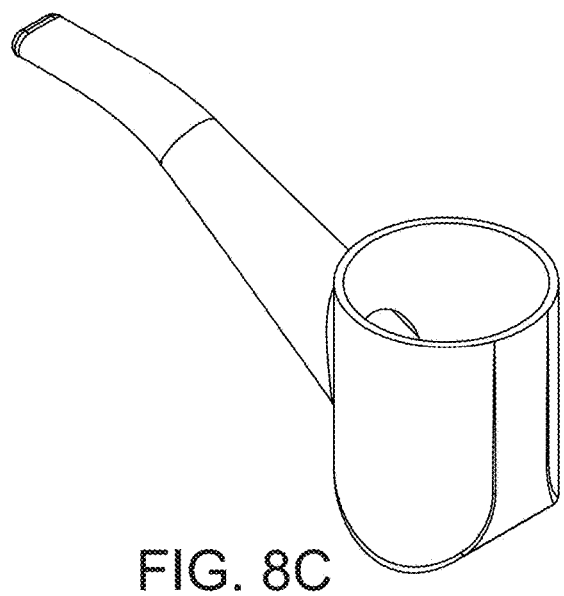
Figure 8D:
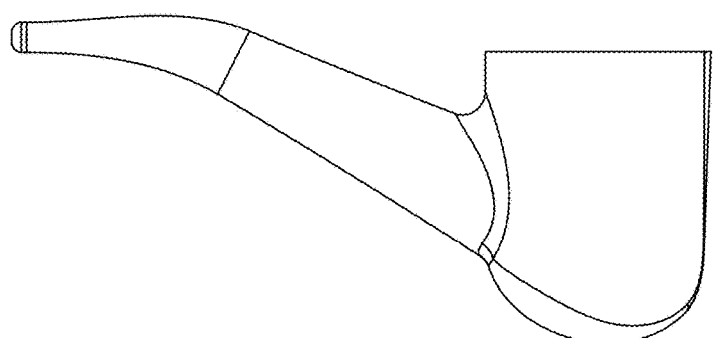
Figure 8E:
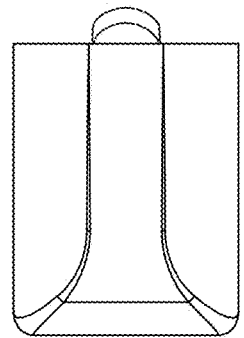

506 configured to receive the vaporization assembly 4 therein. As shown in FIG. 7B, the base portion 5 may also comprises a chamber air seal 513, a chamber bayonet 514, a chamber detection pogo pin 515, a printed circuit board assembly (PCBA) 516, a base electrode 517, and optionally a battery 518. In one embodiment, the base portion 5 comprises a module housing 501 having an insert portion 502 configured to be at least partly received within the receiving area 306 of the mouthpiece housing, the insert portion 502 having one or more sealing regions 503 configured to form a seal between the module housing 501 and the mouthpiece housing, and a battery receiving area 504 disposed within the insert portion and configured to receive a battery for powering the removably attachable vaporization module 2. Embodiments of the base portion 5 comprise a gas flow conduit 505 having an output opening 509 positioned to output the flow of gas from the removably attachable vaporization module 2 to the receiving area of the mouthpiece at an interior side of the seal 503 between the module housing 501 and the mouthpiece housing. In one embodiment, the gas flow conduit 505 has an input opening 510 formed in the bottom wall 508 of the vaporization assembly receiving area 506 of the base portion 5, and is configured to be directly engaged to and/or aligned with at least one of the one or more vaporization assembly outlets 406 of the vaporization assembly 4 (not shown). An embodiment of the gas flow path is depicted via dashed lines. In yet another embodiment, the gas flow conduit 505 extends from the input opening formed in the bottom wall 508 of the vaporization assembly receiving area 506 to the output opening 509, and as shown in FIGS. 6B and 6C, the output opening 509 of the gas flow conduit 505 is formed on an outer surface 512 of the insert portion 502 of the module housing 501 and is radially external to the input opening 510.

Figure 9A:
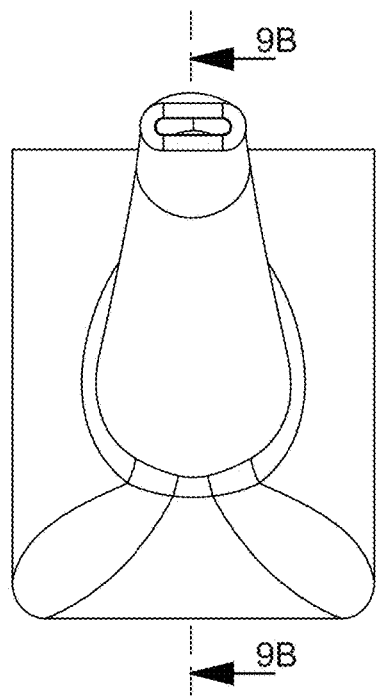
FIG. 9A is a perspective view of the mouthpiece of FIGS. 8A-8E.
Figure 9B:
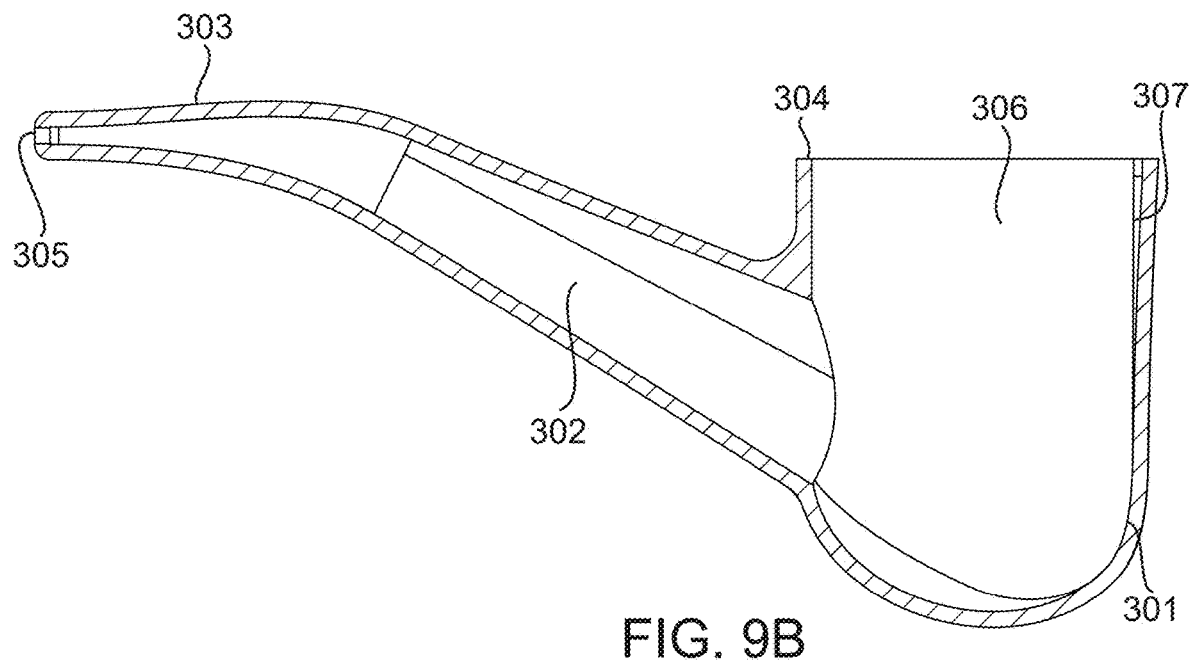
FIG. 9B is a cross-sectional view of FIG. 9A.

Referring to FIGS. 8A-8E, different views of an embodiment of the mouthpiece 3 is shown. A front view and a cross-sectional view are further provided in FIGS. 9A-9B. According to one embodiment, the mouthpiece 3 comprises a mouthpiece housing 301 at least partly defining an interior chamber 302 having a first end 303 and a second end 304, an inhalation outlet 305 formed in the mouthpiece housing 301 at the first end 303 of the interior chamber 303302, and a receiving area 306 for receiving the removably attachable vaporization module 2 that is battery powered, at the second end of the interior chamber 304 within the mouthpiece housing 301. According to embodiments herein, in operation of the portable electronic vaporizing device 1, the flow of gas having the vaporized product entrained therein is passed through the gas flow conduit 505 of the base portion 5 and received into the receiving area 306 of the mouthpiece 3 from the output opening of the gas flow conduit 505, and is passed along the interior chamber 302 of the mouthpiece 3 to the inhalation outlet 305. While the mouthpiece depicted herein is in the shape of a pipe, it should be understood that other mouthpiece shapes and forms are also contemplated herein.

In one embodiment, the battery receiving area 504 of the insert portion is configured to be entirely received within the receiving area 306 of the mouthpiece 3, such that a battery received in the battery receiving area 504 is enclosed by the walls of the mouthpiece 3. In another embodiment, at least a portion of the vaporization assembly 4 connects to the base portion 5 at an exterior side of the seal formed between the module housing 501 and the mouthpiece housing 301. For example, the vaporization assembly 4 may be attached to the base portion 5 at a location that is positioned above the sealing regions 503 that seal the base portion of the removably attachable vaporization module 2 to the mouthpiece, such that the vaporization assembly is located above the mouthpiece. In yet another embodiment, at least a portion of the battery receiving area 504 of the removably attachable vaporization module 2 is configured to be received in the receiving area 306 at an interior side of the seal formed between the module housing 501 and the mouthpiece housing 301. For example, the battery receiving area 504 may be partly or entirely contained within the mouthpiece housing.

Referring to FIGS. 7A-7B and 9A-9B, according to embodiments herein, the one or more sealing regions 503 of the removably attachable vaporization module 2 comprise one or more sealing rings 511 provided about a circumference of an outer surface 512 of the insert portion 502, and which engage an inner surface 307 of the mouthpiece housing 301 in the receiving area 306 to form the seal between the insert portion 502 of the module housing 501 and the inner surface 307 of the mouthpiece housing 301. In yet another embodiment, the seal formed between the module housing 501 and mouthpiece housing 301 at least partly defines the interior chamber 302 of the mouthpiece 3 for flow of the gas having the vaporized product entrained therein from the receiving area 306 to the inhalation outlet 305.

Figure 10A:
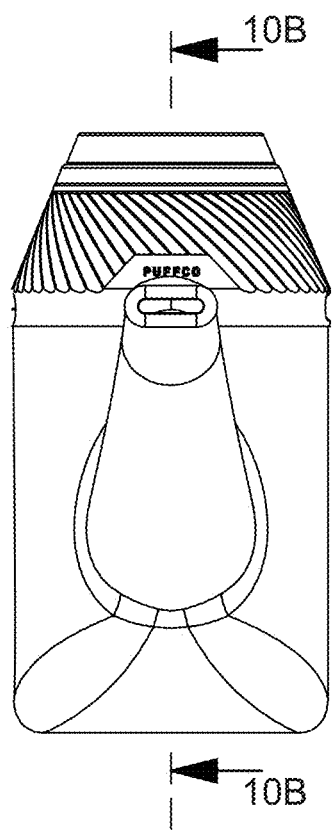
FIG. 10 A is a perspective view.
FIG. 10B is a cross-sectional view, of an embodiment of a device, with FIG. 10B providing a representative gas flow path within the device 1, the gas flow path being illustrated via dashed lines and arrows.
Figure 10B:
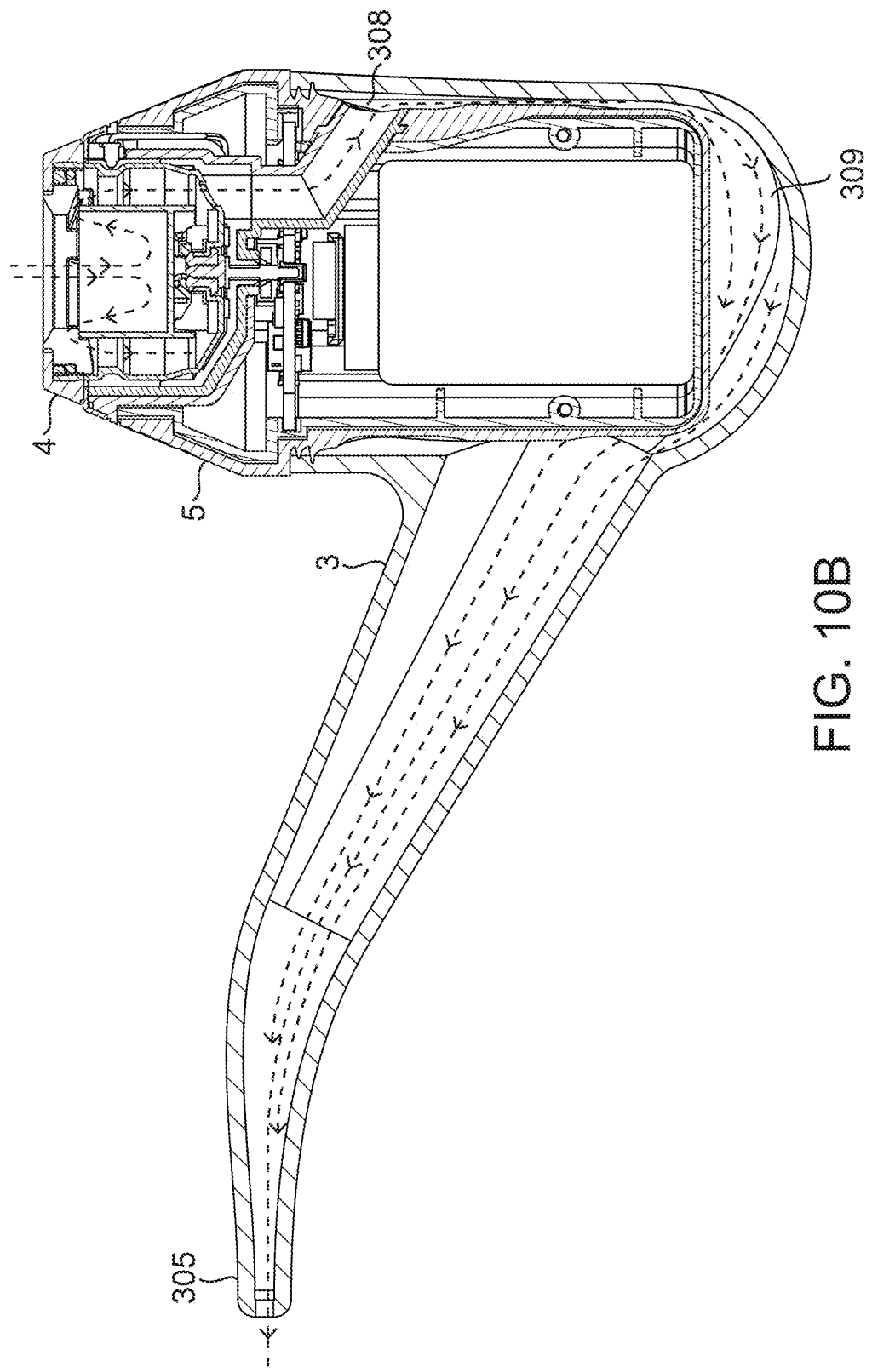
Figure 11A:
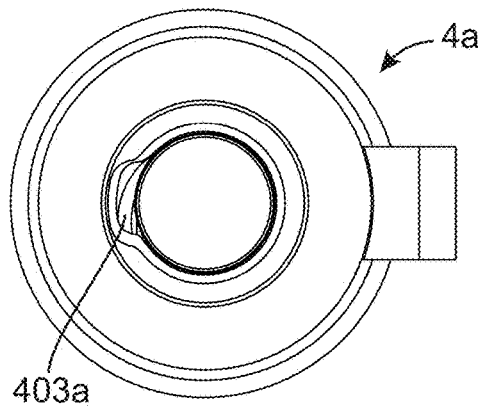
FIGS. 11A-11E show various views of another embodiment of a vaporization assembly.
Figure 11B:
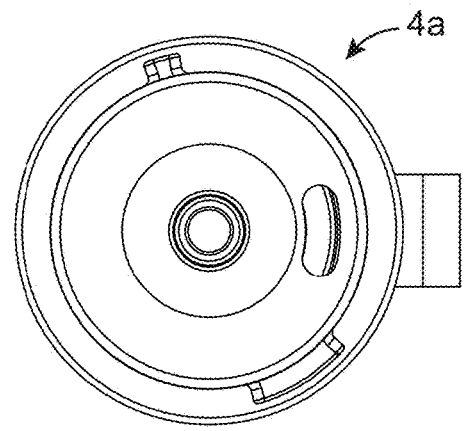
Figure 11C:
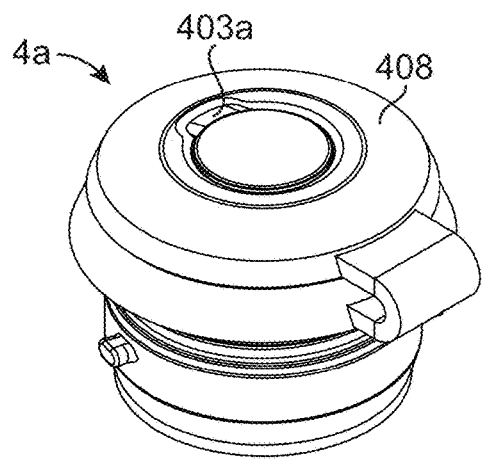
Figure 11D:
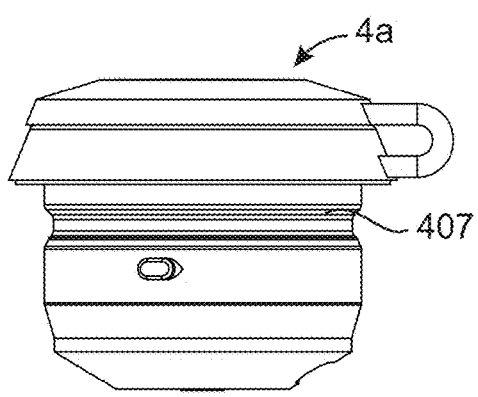
Figure 11E:
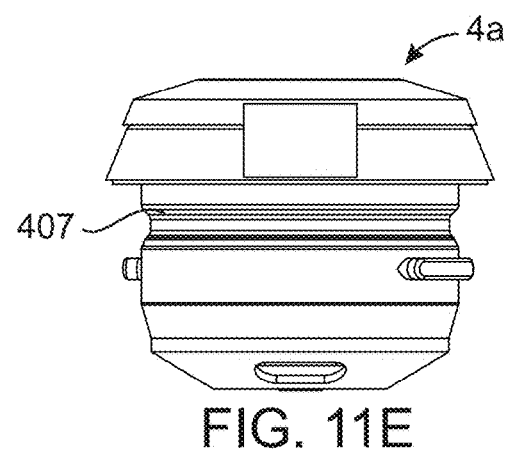
Figure 12A:
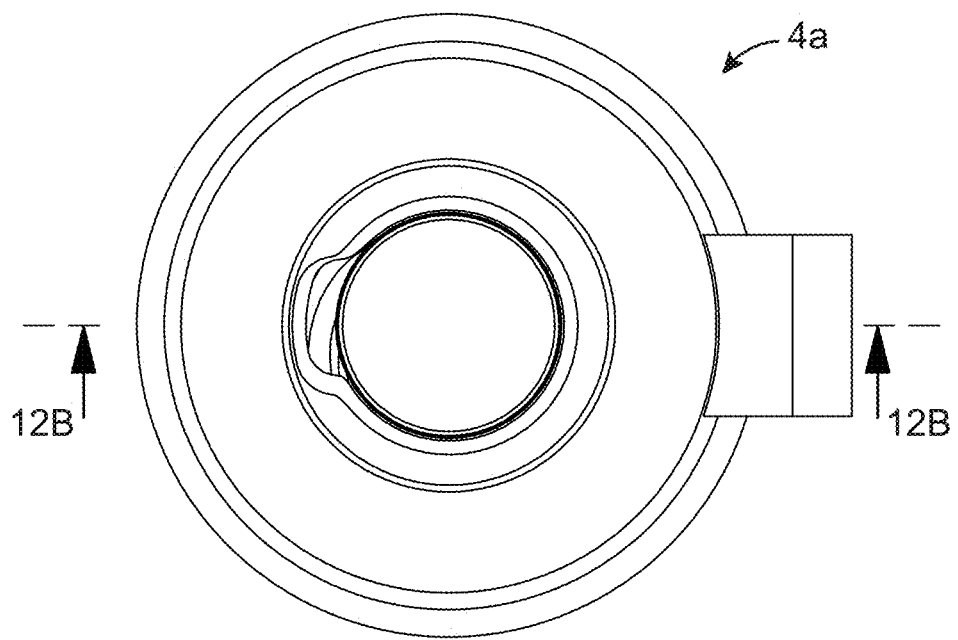
FIG. 12A is a top view of the embodiment of the vaporization assembly of FIGS. 11A-11E and FIG. 12B is a cross-sectional view of FIG. 12A.
Figure 12B:
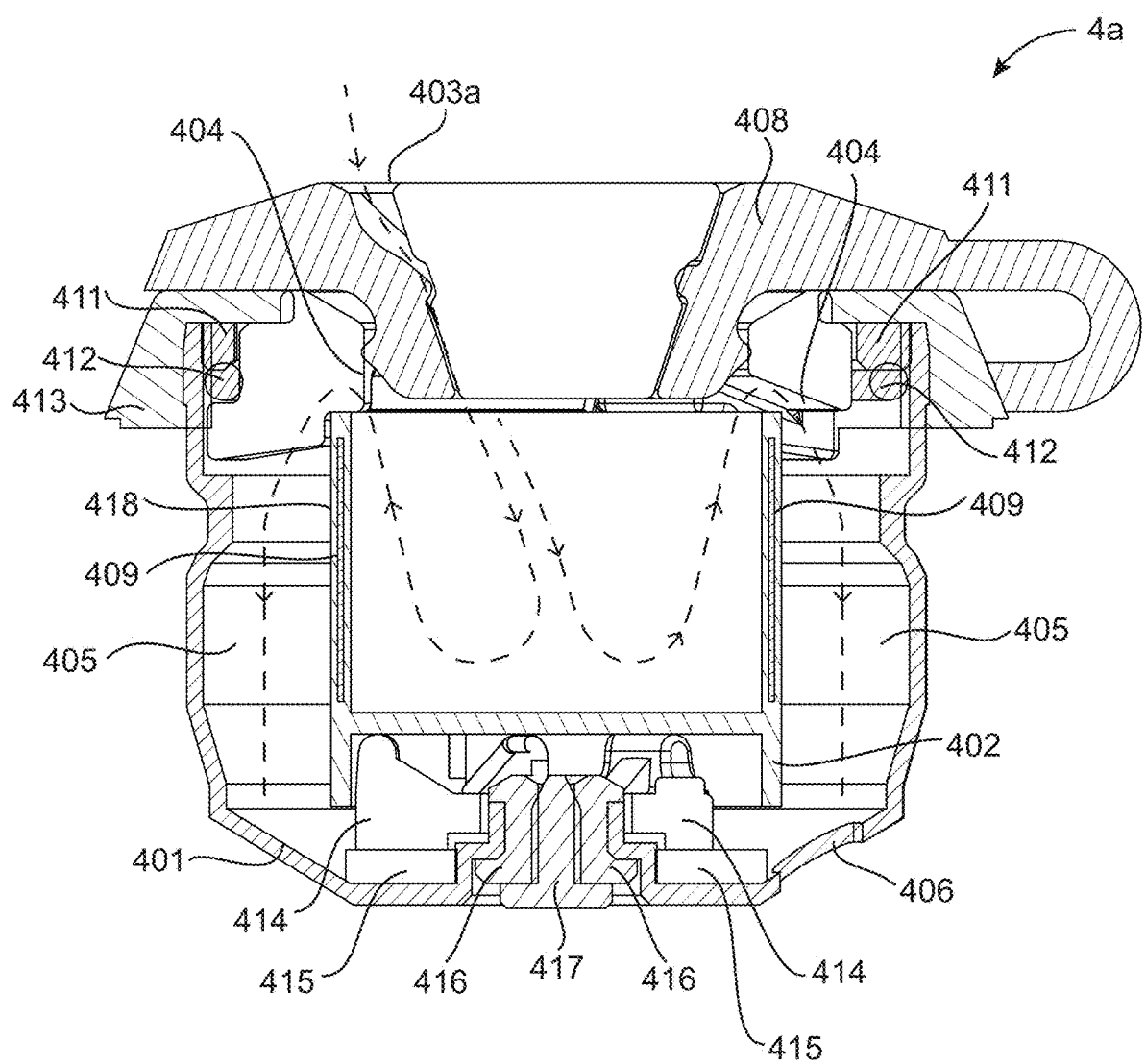
Figure 13A:
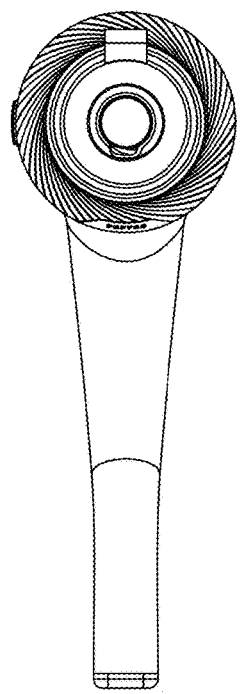
FIGS. 13A-13E show various view of an embodiment of an assembled device.
Figure 13B:
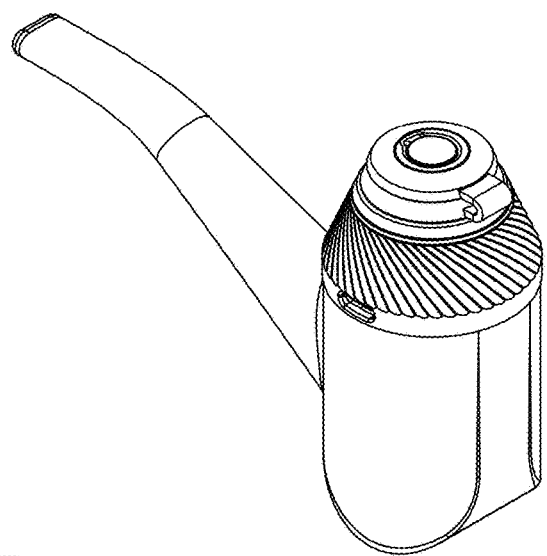
Figure 13C:
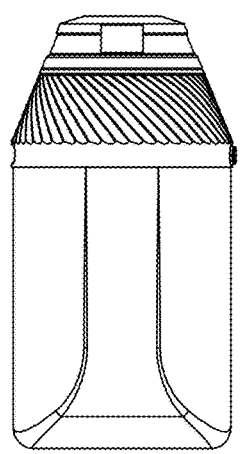
Figure 13D:
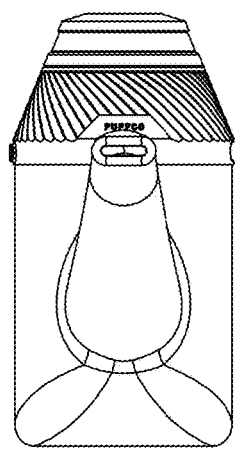
Figure 13E:
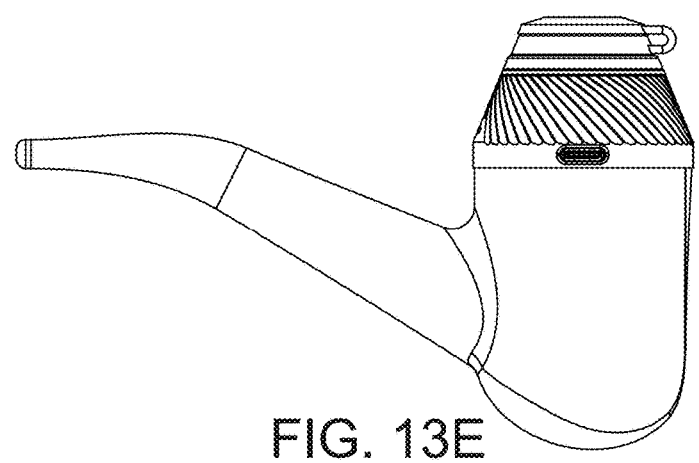

Referring to FIG. 10B, a representative gas flow path within the device 1 is illustrated in a cross-sectional view. A flow of ambient air enters the vaporization assembly 4 through the inlet, carries the vapor formed by the heated vaporable product in the refillable container, then passes through one or more refillable container outlets located near the top edge of the refillable container and enters into the internal gas flow passage, and next leaves the vaporization assembly 4 through one or more vaporization assembly outlets, subsequently passes through the gas flow conduit of the base portion and enters the space between the module housing and the mouthpiece housing, which is also below the one or more sealing regions. The vapor travels along the interior chamber toward the inhalation outlet, and can be inhaled by a user.

In one embodiment, at least a portion of the interior chamber 302 of the mouthpiece 3 is defined by a passage formed between portions of the mouthpiece housing 301 and the surfaces of the insert portion 502. In yet another embodiment, in operation of the device 1, the flow of gas having vaporized product entrained therein is flowed past at least a portion of the battery receiving area 504 of the insert portion 502 before reaching the inhalation outlet 305. For example, as the insert portion comprising the battery receiving area is disposed within the mouthpiece housing, and in between the vaporization assembly and the inhalation outlet, gas exiting the vaporization assembly flows past the battery receiving area of the insert portion as it travels towards the inhalation outlet.

In one embodiment, the output opening 509 of the gas flow conduit 505 is positioned to output the flow of gas from the removably attachable vaporization module to one or more of: (i) a region 308 of the receiving area adjacent the module housing 501, and between the module housing 501 and the mouthpiece housing 301; and (ii) a region 309 of the receiving area below the module housing 501.

In a certain embodiment of the device disclosed herein, the refillable container is disposed above the battery receiving area of the insert portion; the inlet to the refillable container has a diameter of at least 5 mm; and/or the inlet to the refillable container is disposed above the receiving area of the mouthpiece.

Figure 14A:
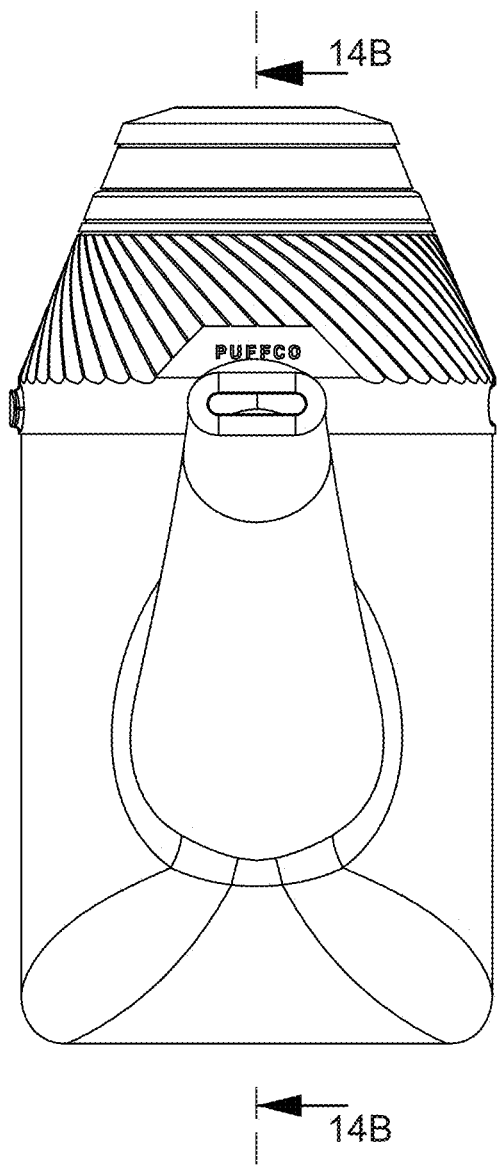
FIG. 14A is a front view of the embodiment of the assembled device of FIGS. 13A-13E.
Figure 14B:
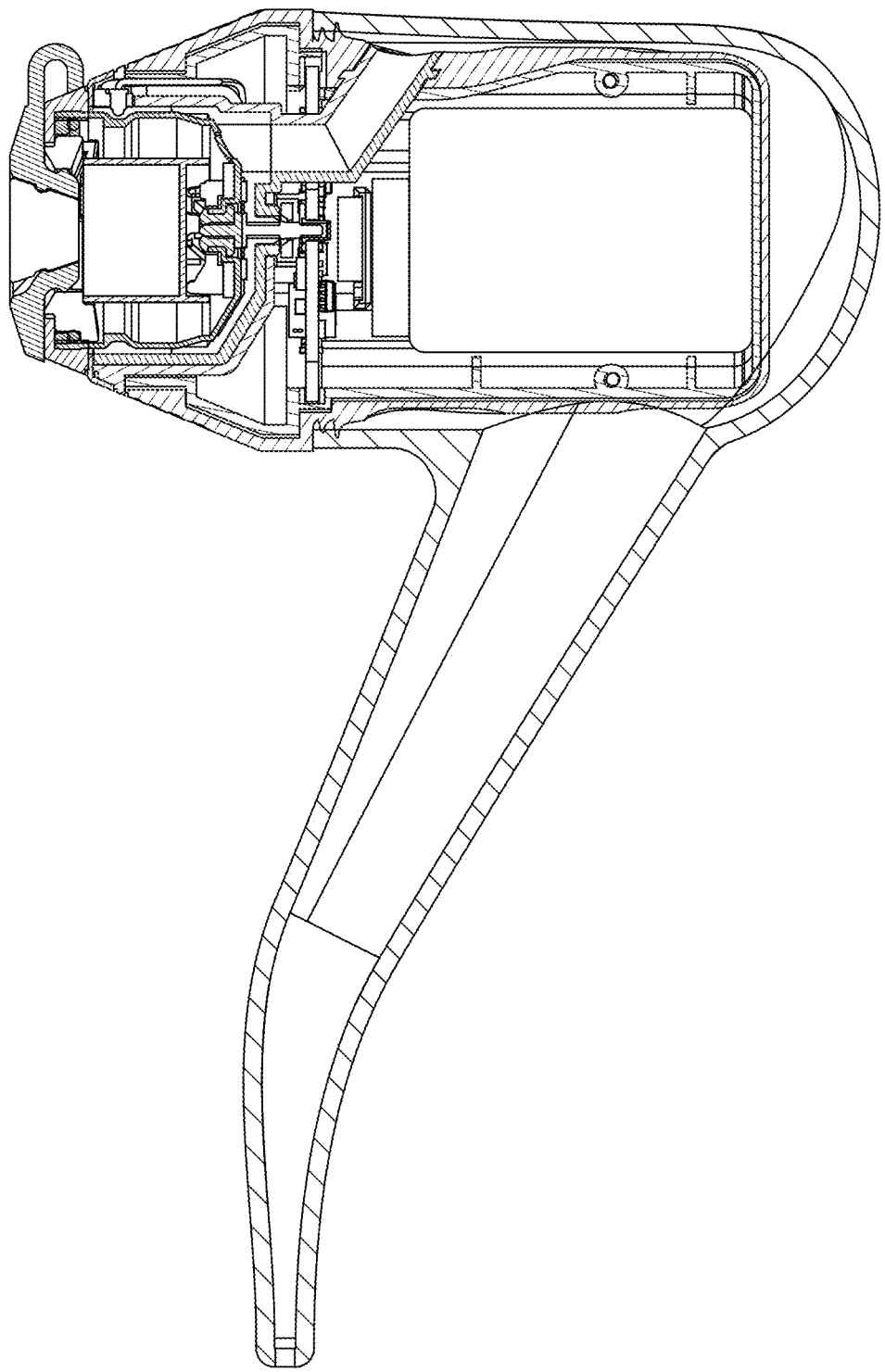
FIG. 14B is a cross-sectional view of FIG. 14A.

In one embodiment, to increase the efficiency of the vaporization, an alternative design of the vaporization assembly can be used. As shown in FIGS. 11A-11E and 12A-12B, the vaporization assembly 4a has a cap 408 to form a closed space with the refillable container 402. Instead of the relatively wide-open inlet 403, a flow of ambient air enters the vaporization assembly 4a through a small air inlet 403a on the cap 408, carries the vapor formed by the heated vaporable product in the refillable container 402, then passes through one or more refillable container outlets 404 located near the top edge of the refillable container 402 and enters into the internal gas flow passage 405, and eventually leaves the vaporization assembly 4 through the gas flow conduit 406. An embodiment of the gas flow path within the vaporization assembly 4 is illustrated in dashed line. A cross-section view of the assembled device 1 equipped with the vaporization assembly 4a is shown in FIGS. 14A-14B. The gas flow path within the device 1 sequentially passing through the base portion and the mouthpiece is, in certain embodiments essentially the same as illustrated in FIGS. 10A-10B, and therefore is not shown in details.

According to embodiments herein, one or more airtight seals are formed between the base portion 5 and/or the vaporization assembly 4 (4a) and the mouthpiece 3, so as to create an airtight gas flow path between from the vaporization assembly 4 (4a), through the gas flow conduit 505 in the base portion 5, and to the mouthpiece 3. In the embodiments as shown, the gas flow conduit 505 in the base portion separates a vaporization assembly internal gas flow path from a mouthpiece internal flow path.

Figure 3B:
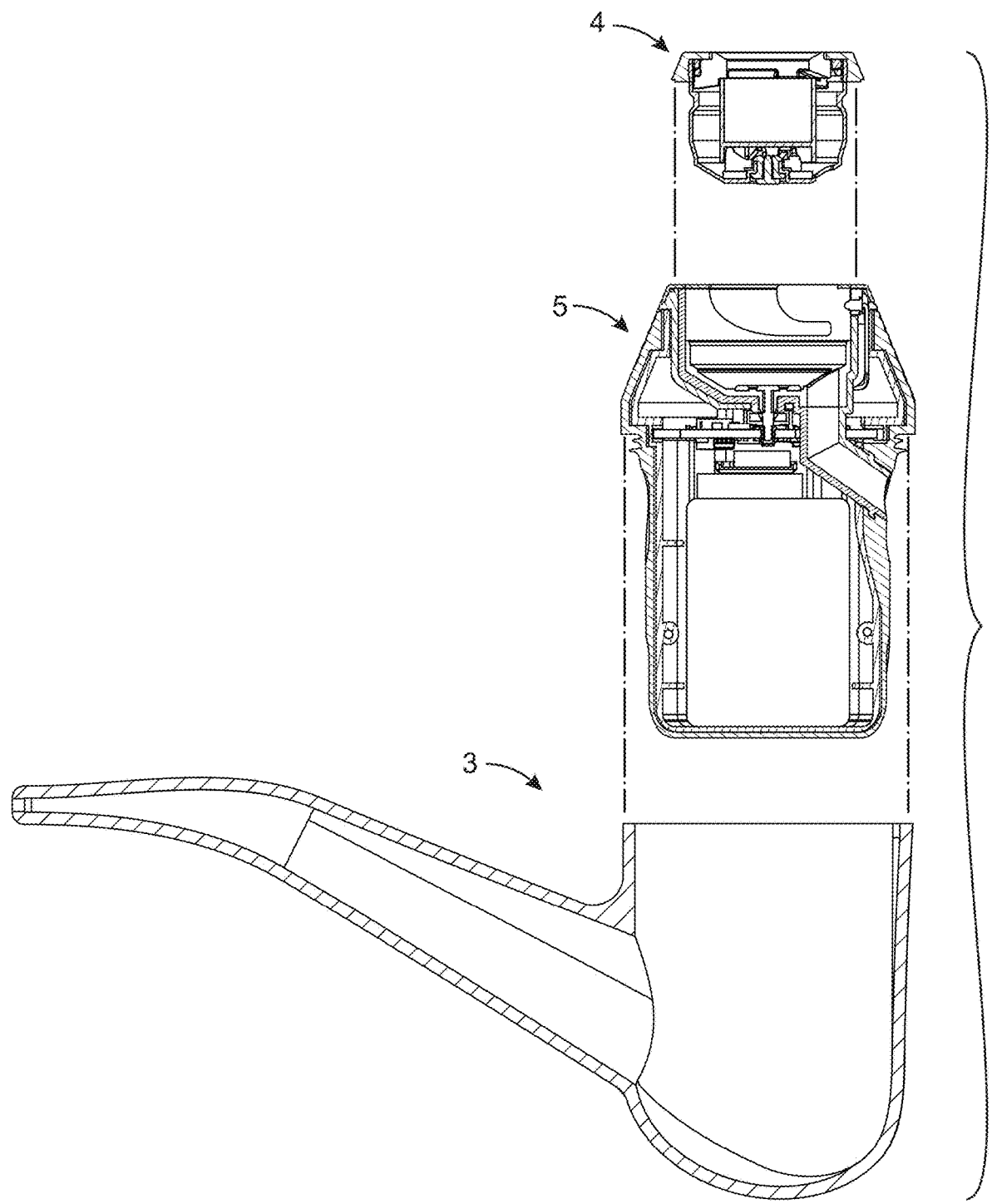
FIG. 3B is a cross-sectional side view of FIG. 3A.
Figure 4A:
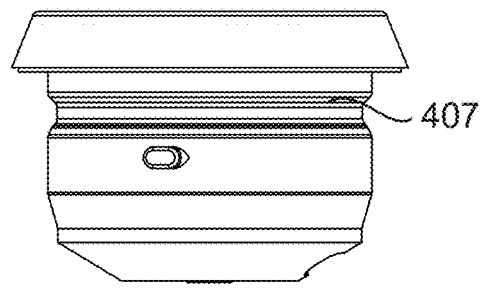
FIGS. 4A-4E show an embodiment of a vaporization assembly in various views.
Figure 4B:
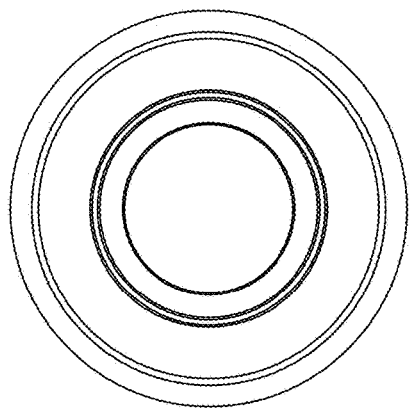
Figure 4C:
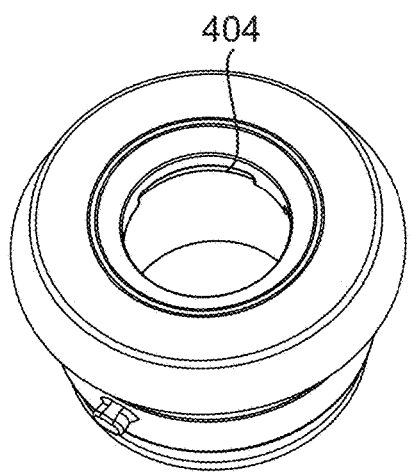
Figure 4D:
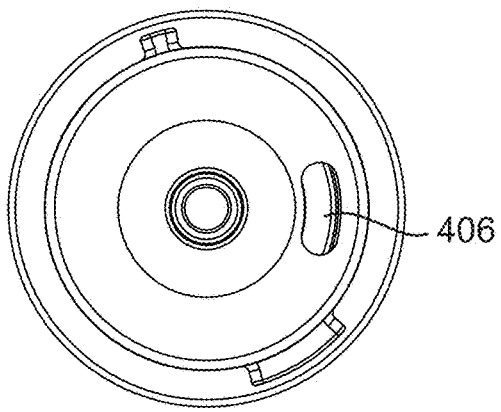
Figure 4E:
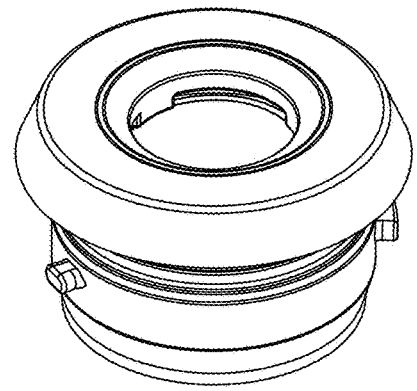

In one embodiment, the vaporization assembly is removably attachable to the base portion via a fastening feature that allows for repeated removal and re-insertion of the vaporization assembly into the base portion. For example, the vaporization assembly may be removable by simply lifting or twisting. In one embodiment, as shown in FIGS. 2 and 3A-3B, the vaporization assembly 4 is attachable/removable by simply inserting into or lifting from the base portion 5. In yet another embodiment, as shown in FIGS. 4A-4E, 5A-5B and 11A-11E, the vaporization assembly 4 (4a) has a fastening feature 407 that is threaded, and that may be complementary to a threaded socket in the base portion 5, so the vaporization assembly can be screwed into the threaded socket of the base portion. In yet another embodiment the vaporization assembly may connect to the base portion via a magnet, span mechanism or other fastening feature. According to embodiments herein, the fastening feature may be located on the base portion, and/or the fastening feature may be located on one or more of the vaporization assembly and mouthpiece, and/or the components may have mutually complementary fastening features that allow for repeatable removal and re-attachment of the vaporization assembly and/or mouthpiece to the base portion.

According to another aspect of the present disclosure, a method of using the portable electronic vaporizing device disclosed herein is provided. For example, the method may comprise: inserting the removably attachable vaporization module into the receiving area of the mouthpiece; providing vaporizable product to the refillable container of the removably attachable vaporization module; activating the heating device to heat the vaporizable product in the refillable container to at least partly vaporize the product; and inhaling gas entrained with the vaporizable product from the inhalation outlet of the mouthpiece. In another embodiment, the method may further comprise assembling the removably attachable vaporization module by inserting the removably attachable atomizer assembly into the receiving area of the base portion and aligning one or more of the vaporization assembly outlets with the gas flow conduit, either before or after insertion of the base portion of the removably attachable vaporization module into the receiving area of the mouthpiece.

According to yet another aspect of the invention, a removably attachable base portion of a vaporization module is provided for vaporizing a vaporizable product in a portable vaporizing device having a receiving body to receive the removably attachable base portion in a receiving area thereof. The removably attachable base portion comprises: a housing having an insert portion configured to be at least partly received within the receiving area of the receiving body, the insert portion having one or more sealing regions configured to form a seal between the housing and one or more walls of the receiving body, and a battery receiving area disposed within the insert portion and configured to receive a battery for powering the vaporization module; and a gas flow conduit having an output opening positioned to output the flow of gas from the removably attachable base portion to the receiving area of the receiving body at an interior side of the seal between the housing and the one or more walls of the receiving body.

In one embodiment, the removably attachable vaporization module may further comprise a vaporization assembly. The vaporization assembly may comprise a vaporization assembly housing, a refillable container configured to receive a vaporizable product within the vaporization assembly housing, a heating device configured to be electrically connected to the battery and transfer energy to the vaporizable product in the refillable container to heat the vaporizable product and form a vaporized product therefrom, an inlet configured to introduce gas into the refillable container, one or more refillable container outlets configured to receive a flow of gas having the vaporized product entrained therein from the refillable container, one or more vaporization assembly outlets configured to provide the flow of gas received from the refillable container outlets to the input opening of the gas flow conduit in the base portion. Optionally, the vaporization assembly is removably attachable to the base portion. According to yet another embodiment, the removably attachable vaporization module is configured to be removably attached to a receiving body comprising a mouthpiece of a portable vaporizing device.

EQUIVALENTS

While specific embodiments have been discussed, the above specification is illustrative, and not restrictive. Many variations will become apparent to those skilled in the art upon review of this specification. The full scope of the embodiments should be determined by reference to the claims, along with their full scope of equivalents, and the specification, along with such variations.

What is claimed is:

1. A portable electronic vaporizing device comprising a removably attachable vaporization module, and a mouthpiece configured to receive a flow of gas having vaporized product entrained therein from the removably attachable vaporization module, wherein
    the mouthpiece comprises:
        a mouthpiece housing at least partly defining an interior chamber;
        an inhalation outlet formed in the mouthpiece housing; and a receiving area for receiving the removably attachable vaporization module that is battery powered, in the interior chamber of the mouthpiece housing, and the removably attachable vaporization module comprises:
- a base portion comprising:
  - a module housing having an insert portion configured to be at least partly received within the receiving area of the mouthpiece housing, the insert portion having one or more sealing regions configured to form a seal between the module housing and the mouthpiece housing, and a battery receiving area disposed within the insert portion and configured to receive a battery for powering the removably attachable vaporization module; and
  - a gas flow conduit having an input opening and an output opening positioned to output the flow of gas from the removably attachable vaporization module to the receiving area of the mouthpiece at an interior side of the seal between the module housing and the mouthpiece housing, and
- a vaporization assembly comprising;
  - a vaporization assembly housing;
  - a refillable container configured to receive a vaporizable product within the vaporization assembly housing;
  - a heating device configured to be electrically connected to the battery and transfer energy to the vaporizable product in the refillable container to heat the vaporizable product and form a vaporized product therefrom;
  - an inlet configured to introduce gas into the refillable container;
  - one or more refillable container outlets configured to receive the flow of gas having the vaporized product entrained therein from the refillable container; and
  - one or more vaporization assembly outlets configured to provide the flow of gas received from the refillable container outlets to the input opening of the gas flow conduit in the base portion, wherein in operation of the portable electronic vaporizing device, the flow of gas having the vaporized product entrained therein is passed through the gas flow conduit and received into the receiving area of the mouthpiece from the output opening of the gas flow conduit, and is passed along the interior chamber of the mouthpiece to the inhalation outlet.

2. The portable electronic vaporizing device according to claim 1, wherein the battery receiving area is configured to be entirely received within the receiving area of the mouthpiece, such that a battery received in the battery receiving area is enclosed by the walls of the mouthpiece.

3. The portable electronic vaporizing device according to claim 1, wherein the mouthpiece housing at least partly defines an interior chamber having a first end and a second end, the inhalation outlet is formed in the mouthpiece housing in the first end of the interior chamber, and the receiving area for receiving the battery powered, removably attachable vaporization module is at the second end of the interior chamber within the mouthpiece housing.

4. The portable electronic vaporizing device according to claim 1, wherein the vaporization assembly comprises an internal gas flow passage within the vaporization assembly housing configured to provide the flow of gas having the vaporized product entrained therein from the one or more refillable container outlets towards the one or more vaporization assembly outlets.

5. The portable electronic vaporizing device according to claim 1, wherein at least one of the one or more vaporization assembly outlets is aligned with the input opening of the gas flow conduit in the base portion.

6. The portable electronic vaporizing device according to claim 1, wherein at least a portion of the vaporization assembly connects to the base portion at an exterior side of the seal formed between the module housing and the mouthpiece housing.

7. The portable electronic vaporizing device according to claim 1, wherein the vaporization assembly is removably attachable to the base portion.

8. The portable electronic vaporizing device according to claim 7, wherein the base portion comprises sidewalls and a bottom wall defining a vaporization assembly receiving area configured to receive the vaporization assembly therein.

9. The portable electronic vaporizing device according to claim 8, wherein the one or more vaporization assembly outlets are at a lower region of the vaporization assembly housing that is configured to be engaged to the input opening of the gas flow conduit, the input opening being formed in the bottom wall of the vaporization assembly receiving area of the base portion.

10. The portable electronic vaporizing device according to claim 9, wherein the gas flow conduit extends from the input opening formed in the bottom wall of the vaporization assembly receiving area to the output opening, and wherein the output opening of the gas flow conduit is formed on an outer surface of the insert portion of the module housing and is radially external to the input opening.

11. The portable electronic vaporizing device according to claim 1, wherein the inlet and the one or more refillable container outlets of the vaporization assembly are located towards a top of the refillable container, and wherein the one or more refillable container outlets of the vaporization assembly are located radially external to the inlet of the refillable container.

12. The portable electronic vaporizing device according to claim 4, wherein the internal gas flow passage is defined between the vaporization assembly housing and walls of the refillable container, radially external to the refillable container, and wherein the internal gas flow passage redirects the flow of gas received from the one or more refillable container outlets in a direction towards the base portion of the battery powered, removably attachable vaporization module.

13. The portable electronic vaporizing device according to claim 1, wherein the one or more sealing regions comprise one or more sealing rings provided about a circumference of an outer surface of the insert portion, and which engage an inner surface of the mouthpiece housing in the receiving area to form the seal between the insert portion of the module housing and the inner surface of the mouthpiece housing.

14. The portable electronic vaporizing device according to claim 1, wherein the seal formed between the module housing and mouthpiece housing at least partly defines the interior chamber of the mouthpiece for flow of the gas having the vaporized product entrained therein from the receiving area to the inhalation outlet.

15. The portable electronic vaporizing device according to claim 1, wherein at least a portion of the battery receiving area of the removably attachable vaporization module is configured to be received in the receiving area at an interior side of the seal formed between the module housing and the mouthpiece housing.

16. The portable electronic vaporizing device according to claim 1, wherein the heating device comprises at least one of a heating plate, a heating ring, and a heating element, and is capable of conductively heating the vaporizable product in the refillable container.

17. The portable electronic vaporizing device according to claim 1, wherein at least a portion of the interior chamber of the mouthpiece is defined by a passage formed between portions of the mouthpiece housing and the surfaces of the insert portion.

18. The portable electronic vaporizing device according to claim 1, wherein in operation of the device, the flow of gas having vaporized product entrained therein is flowed past at least a portion of the battery receiving area of the insert portion before reaching the inhalation outlet.

19. The portable electronic vaporizing device according to claim 1, wherein the output opening of the gas flow conduit is positioned to output the flow of gas from the removably attachable vaporization module to one or more of: (i) a region of the receiving area adjacent the module housing, and between the module housing and the mouthpiece housing; and (ii) a region of the receiving area below the module housing.

20. The portable electronic vaporizing device according to claim 1, wherein:
the refillable container is disposed above the battery receiving area of the insert portion;
the inlet to the refillable container has a diameter of at least 5 mm; and/or
the inlet to the refillable container is disposed above the receiving area of the mouthpiece.

21. A method of using the portable electronic vaporizing device according to claim 1, comprising:
inserting the removably attachable vaporization module into the receiving area of the mouthpiece;
providing vaporizable product to the refillable container of the removably attachable vaporization module;
activating the heating device to heat the vaporizable product in the refillable container to at least partly vaporize the product; and
inhaling gas entrained with the vaporizable product from the inhalation outlet of the mouthpiece.

22. The method according to claim 21, further comprising assembling the removably attachable vaporization module by inserting the removably attachable atomizer assembly into the receiving area of the base portion and aligning one or more of the vaporization assembly outlets with the gas flow conduit, either before or after insertion of the base portion of the removably attachable vaporization module into the receiving area of the mouthpiece.

23. A removably attachable base portion of a vaporization module for vaporizing a vaporizable product in a portable vaporizing device having a receiving body to receive the removably attachable base portion in a receiving area thereof, the removably attachable base portion comprising:
a housing having an insert portion configured to be at least partly received within the receiving area of the receiving body, the insert portion having one or more sealing regions configured to form a seal between the housing and one or more walls of the receiving body, and a battery receiving area disposed within the insert portion and configured to receive a battery for powering the vaporization module; and
a gas flow conduit having an output opening positioned to output the flow of gas from the removably attachable base portion to the receiving area of the receiving body at an interior side of the seal between the housing and the one or more walls of the receiving body.

24. A removably attachable vaporization module comprising the removably attachable base portion of claim 23, the removably attachable vaporization module further comprising:
a vaporization assembly comprising;
a vaporization assembly housing;
a refillable container configured to receive a vaporizable product within the vaporization assembly housing;
a heating device configured to be electrically connected to the battery and transfer energy to the vaporizable product in the refillable container to heat the vaporizable product and form a vaporized product therefrom;
an inlet configured to introduce gas into the refillable container;
one or more refillable container outlets configured to receive a flow of gas having the vaporized product entrained therein from the refillable container;
one or more vaporization assembly outlets configured to provide the flow of gas received from the refillable container outlets to the input opening of the gas flow conduit in the base portion, and
optionally wherein the vaporization assembly is removably attachable to the base portion.

25. The removably attachable vaporization module of claim 24, configured to be removably attached to a receiving body comprising a mouthpiece of a portable vaporizing device.

* * * * *